(12) United States Patent
Fink et al.

(10) Patent No.: US 8,487,079 B2
(45) Date of Patent: Jul. 16, 2013

(54) USE OF MITOCHONDRIA-TARGETED ELECTRON SCAVENGERS AS ANTI-INFLAMMATORY AGENTS

(75) Inventors: Mitchell P. Fink, Pittsburgh, PA (US); Peter Wipf, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 921 days.

(21) Appl. No.: 12/188,369

(22) Filed: Aug. 8, 2008

(65) Prior Publication Data
US 2009/0042808 A1 Feb. 12, 2009

Related U.S. Application Data

(60) Provisional application No. 60/954,661, filed on Aug. 8, 2007.

(51) Int. Cl.
*C07K 9/00* (2006.01)
(52) U.S. Cl.
USPC .......... 530/330; 530/331; 530/332; 424/9.33; 424/9.34
(58) Field of Classification Search
USPC ................. 530/331, 317, 330, 332; 424/9.33, 424/9.34
See application file for complete search history.

(56) References Cited

U.S. PATENT DOCUMENTS

| | | | | |
|---|---|---|---|---|
| 5,380,758 | A * | 1/1995 | Stamler et al. | 514/562 |
| 5,908,756 | A * | 6/1999 | Snyder et al. | 435/7.1 |
| 6,075,121 | A | 6/2000 | Simon et al. | |
| 6,331,532 | B1 | 12/2001 | Murphy et al. | |
| 6,656,498 | B1 | 12/2003 | Gao | |
| 6,696,038 | B1 | 2/2004 | Mahato et al. | |
| 6,749,863 | B1 | 6/2004 | Chang et al. | |
| 2005/0107366 | A1 | 5/2005 | Carney et al. | |
| 2005/0169904 | A1 | 8/2005 | Payne | |
| 2005/0245487 | A1 | 11/2005 | Murphy et al. | |
| 2007/0161544 | A1 | 7/2007 | Wipf et al. | |
| 2007/0161573 | A1 | 7/2007 | Wipf et al. | |
| 2008/0153748 | A1* | 6/2008 | Jaynes | 514/12 |

OTHER PUBLICATIONS

Jian-Jun, Am J Pathol 169(6), 1953-1964, 2006.*
Lirk, Philipp (Current Drug Targets. Inflammation and Allergy 1(1), 89-108, 2002).*
Abashkin YG, Burt SK. (salen)MnIII compounds as nonpeptidyl mimics of catalase. Mechanism-based tuning of catalase activity: a theoretical study. Inorg Chem. Mar. 7, 2005;44(5):1425-32.
Andreyev AY, Kushnareva YE, Starkov AA. Mitochondrial metabolism of reactive oxygen species. Biochemistry (Mosc). Feb. 2005;70(2):200-14.
Baker RD, et al. Polarized Caco-2 cells. Effect of reactive oxygen metabolites on enterocyte barrier function. Dig Dis Sci. Mar. 1995;40(3):510-8.
Balaban RS, Nemoto S, Finkel T. Mitochondria, oxidants, and aging. Cell. Feb. 25, 2005;120(4):483-95.
Banan A, et al. Activation of delta-isoform of protein kinase C is required for oxidant-induced disruption . . . J Pharmacol Exp Ther. Oct. 2002;303(1):17-28.
Batinic-Haberle I, et al. New PEG-ylated Mn(III) porphyrins approaching catalytic activity of SOD enzyme. Dalton Trans. Jan. 28, 2006;(4):617-24.
Berry S. Endosymbiosis and the design of eukaryotic electron transport. Biochim Biophys Acta—Bioenergetics. Sep. 30, 2003;1606(1-3):57-72.
Bottcher CFJ, et al. A rapid and sensitive sub-micro phosphorous determination. Anal Chim Acta. 1961 24, 203-204.
Butler MS, Buss AD. Natural products—the future scaffolds for novel antibiotics? Biochem Pharmacol. Mar. 30, 2006;71(7):919-29.
Cairns CB. Rude unhinging of the machinery of life: metabolic approaches to hemorrhagic shock. Curr Opin Crit Care. Dec. 2001;7(6):437-43.
Clement AM et al. Wild-type nonneuronal cells extend survival of SOD1 mutant motor neurons in ALS mice. Science. Oct. 3, 2003;302(5642):113-7.
Cuzzocrea S, et al. Effects of tempol, a membrane-permeable radical scavenger, in a gerbil model of brain injury. Brain Res. Sep. 1, 2000;875(1-2):96-106.
Delude RL, et al. Novel Nitroxide-Gramicidin Conjugates Target Mitochondria ROS Production and Decrease Inflammation. Society of Critical Care Medicine's 37th Critical Care Congress Abstracts. Crit Care Med. Dec. 2007;35(12 Suppl):A18. (Abstract 72).
Dolder M, et al. Mitochondrial creatine kinase in contact sites: interaction with porin and adenine nucleotide . . . Biol Signals Recept. Jan.-Apr. 2001;10(1-2):93-111.
Dröge W. Free radicals in the physiological control of cell function. Physiol Rev. Jan. 2002,;82(1):47-95.
Edmonds MK, Abell AD. Design and synthesis of a conformationally restricted trans peptide isostere based on the bioactive conformations . . . J Org Chem. Jun. 1, 2001;66(11):3747-52.
Epperly MW, et al. Manganese superoxide dismutase (SOD2) inhibits radiation induced apoptosis by stabilization of the mitochondrial membrane. Rad Res 2002; 157: 568-577.
Fink MP, et al. Hemigramicidin-TEMPO conjugates: novel mitochondria-targeted antioxidants. Crit Care Med. Sep. 2007;35(9 Suppl):S461-7.
Fink MP, et al. Hemigramicidin-TEMPO conjugates: novel mitochondria-targeted anti-oxidants. Biochem Pharmacol. Sep. 15, 2007;74(6):801-9. Epub May 29, 2007.
Fink MP. Reactive oxygen species as mediators of organ dysfunction caused by sepsis, acute respiratory distress syndrome, or hemorrhagic shock: potential benefits of resuscitation with Ringer's ethyl pyruvate solution. Curr Opin Clin Nutr Metab Care Mar. 2002,5(2):167-74.
Folch J, et al. A simple method for the isolation and purification of total lipids from animal tissues. J. Biol. Chem. 1957 226: 497-509.

(Continued)

*Primary Examiner* — David Lukton
(74) *Attorney, Agent, or Firm* — The Webb Law Firm

(57) ABSTRACT

Provided herein are methods for using mitochondria-targeted electron scavengers as anti-inflammatory agents. The mitochondria-targeted electron scavenger comprises a free radical-scavenging group covalently linked to a mitochondria-targeting group derived from a hemigramicidin moiety. The mitochondria-targeted electron scavenger can be used to treat medical conditions associated with acute or chronic inflammation.

26 Claims, 7 Drawing Sheets

OTHER PUBLICATIONS

Gibson SE, Lecci C. Amino acid derived macrocycles—an area driven by synthesis or application? Angew Chem Int Ed Engl. Feb. 20, 2006;45(9):1364-77.

Gloire G, Legrand-Poels S, Piette J. NF-kappaB activation by reactive oxygen species: fifteen years later. Biochem Pharmacol Nov. 30, 2006;72(11):1493-505.

Guzik TJ, Korbut R, Adamek-Guzik T. Nitric oxide and superoxide in inflammation and immune regulation. J Physiol Pharmacol. Dec. 2003,54(4):469-87.

Hahn SM, et al. Mn(III)-Desferrioxamine superoxide dismutase-mimic: alternative modes of action. Arch. Biochem. Biophy. Jul. 1991; 288(1):215-219.

Hahn SM, Tochner Z, Krishna CM, Glass J, Wilson L, Samuni A, Sprague M, Venzon D, Glatstein E, Mitchell JB, Russo A. Tempol, a stable free radical, is a novel murine radiation protector. Cancer Res. Apr. 1, 1992;52(7):1750-3.

Han X, et al. Proinflammatory cytokines cause NO*-dependent and -independent changes in expression and localization of tight junction proteins . . . Shock. Mar. 2003;19(3):229-37.

He H. Mannopeptimycins, a novel class of glycopeptide antibiotics active against gram-positive bacteria. Appl Microbiol Biotechnol. Jun. 2005;67(4):444-52.

Hoye AT, Davoren JE, Wipf P, Fink MP, Kagan VE. Targeting mitochondria. Acc Chem Res. Jan. 2008;41(1):87-97.

Imai H, et al. Protection from inactivation of the adenine nucleotide translocator during hypoglycaemia-induced apoptosis by mitochondrial . . . Biochem J. May 1, 2003;371(Pt 3):799-809.

Itami C, et al. Superoxide dismutase mimetic activities of metal complexes of . . . Biochem Biophys Res Commun. Dec. 15, 1993;197(2):536-41.

Iverson SL, Orrenius S. The cardiolipin-cytochrome c interaction and the mitochondrial regulation of apoptosis. Arch Biochem Biophys. Mar. 1, 2004;423(1):37-46.

Jelokhani-Niaraki M, Kondejewski LH, Farmer SW, Hancock RE, Kay CM, Hodges RS. Diastereoisomeric analogues of gramicidin S: structure, biological activity and interaction with lipid bilayers. Biochem J. Aug. 1, 2000;349 Pt 3:747-55.

Jiang J, et al. Structural requirements for optimized delivery, inhibition of oxidative stress, and antiapoptotic activity of targeted nitroxides. J Pharmacol Exp Ther. Mar. 2007;320(3):1050-60.

Kagan VE, et al. A role for oxidative stress in apoptosis: oxidation and externalization of phosphatidylserine is required for macrophage clearance of cells undergoing Fas-Mediated Apoptosis. J Immunol. Jul. 1, 2002;169(1):487-99.

Kagan VE, et al. Cytochrome c acts as a cardiolipin oxygenase required for release of proapoptotic factors. Nat Chem Biol. Sep. 2005;1(4):223-32.

Kagan VE, et al. Oxidative lipidomics of apoptosis: redox catalytic interactions of cytochrome c with cardiolipin and phosphatidylserine. Free Radic Biol Med. Dec. 15, 2004;37(12):1963-85.

Kanai A, et al. Differing roles of mitochondrial nitric oxide synthase in cardiomyocytes and urothelial cells. Am J Physiol Heart Circ Physiol. Jan. 2004;286(1):H13-21.

Kanai A, Peterson J. Function and regulation of mitochondrially produced nitric oxide in cardiomyocytes. Am J Physiol Heart Circ Physiol. Jan. 2004;286(1):H11-2.

Kanai A, et al. Mitochondrial targeting of radioprotectants using peptidyl conjugates. Org Biomol Chem. Jan. 21, 2007;5(2):307-9. Epub Dec. 7, 2006.

Kanai AJ, et al. Identification of a neuronal nitric oxide synthase in isolated cardiac mitochondria using electrochemical detection. Proc Natl Acad Sci U S A. Nov. 20, 2001;98(24):14126-31.

Kanai AJ, et al. Manganese superoxide dismutase gene therapy protects against irradiation-induced cystitis. Am J Physiol Renal Physiol. Dec. 2002;283(6):F1304-12.

Kelso GF, et al P. Selective targeting of a redox-active ubiquinone to mitochondria within cells: antioxidant and antiapoptotic properties. J Biol Chem. Feb. 16, 2001;276(7):4588-96.

Kentner R, et al. Early antioxidant therapy with Tempol during hemorrhagic shock increases survival in rats. J Trauma. Nov. 2002;53(5):968-77.

Kondejewski LH, et al. Gramicidin S is active against both gram-positive and gram-negative bacteria. Int J Pept Protein Res Jun. 1996; 47(6):460-66.

Konorev EA, et al. Cell-permeable superoxide dismutase and glutathione peroxidase mimetics afford superior protection against . . . Arch Biochem Biophys. Aug. 15, 1999;368(2):421-8.

Krishna MC, Russo A, Mitchell JB, Goldstein S, Dafni H, Samuni A. Do nitroxide antioxidants act as scavengers of $O_2^-$ or as SOD mimics? J Biol Chem. Oct. 18, 1996;271(42):26026-31.

Lee DL, Hodges RS. Structure-activity relationships of de novo designed cyclic antimicrobial peptides based on gramicidin S. Biopolymers. 2003;71(1):28-48.

Liaw WJ, Chen TH, Lai ZZ, Chen SJ, Chen A, Tzao C, Wu JY, Wu CC. Effects of a membrane-permeable radical scavenger, Tempol, on intraperitoneal sepsis-induced organ injury in rats. Shock. Jan. 2005;23(1):88-96.

Lin SJ, Shyue SK, Hung YY, Chen YH, Ku HH, Chen JW, Tam KB, Chen YL. Superoxide dismutase inhibits the expression of vascular cell adhesion molecule-1 and intracellular cell adhesion molecule-1 induced by tumor necrosis factor-alpha in human endothelial cells through the JNK/p38 pathways. Arterioscler Thromb Vasc Biol. Feb. 2005;25(2):334-40.

Liu H, Colavitti R, Rovira II, Finkel T. Redox-dependent transcriptional regulation. Circ Res. Nov. 11, 2005;97(10):967-74.

Macias CA, Chiao JW, Xiao J, Arora DS, Tyurina YY, Delude RL, Wipf P, Kagan VE, Fink MP. Treatment with a novel hemigramicidin-TEMPO conjugate prolongs survival in a rat model of lethal hemorrhagic shock. Ann Surg. Feb. 2007;245(2):305-14.

Macias CA, Killeen ME, Singh D, Delude RL, Fink MP. A Novel Hemigramicidin-TEMPO Conjugate Has Anti-Inflammatory Effects in Vitro and in Vivo. Society of Critical Care Medicine's 36th Critical Care Congress Abstracts. Crit Care Med. Dec. 2006;34(12):A8. (Abstract 30).

McDonald MC, Zacharowski K, Bowes J, Cuzzocrea S, Thiemermann C. Tempol reduces infarct size in rodent models of regional myocardial ischemia and reperfusion. Free Radic Biol Med. Sep. 1999;27(5-6):493-503.

Nagai H, Noguchi T, Takeda K, Ichijo H. Pathophysiological roles of ASK1-MAP kinase signaling pathways. J Biochem Mol Biol. Jan. 31, 2007,40(1):1-6.

Niccolai N. et al. An investigation of the mechanisms of nitroxide-induced proton relaxation enhancements in biopolymers. J Phys Chem. 1984;88:5689-92.

Nicolas P, et al. Molecular strategies in biological evolution of antimicrobial peptides. Peptides. Nov. 2003;24(11):1669-80.

Nishiyama A, Fukui T, Fujisawa Y, Rahman M, Tian RX, Kimura S, Abe Y. Systemic and Regional Hemodynamic Responses to Tempol in Angiotensin II-Infused Hypertensive Rats. Hypertension. Jan. 2001;37(1):77-83.

Olcott AP, et al. A salen-manganese catalytic free radical scavenger inhibits type 1 diabetes and islet allograft rejection. Diabetes. Oct. 2004;53(10):2574-80.

Pantano C, Reynaert NL, van der Vliet A, Janssen-Heininger YM. Redox-sensitive kinases of the nuclear factor-kappaB signaling pathway. Antioxid Redox Signal. Sep.-Oct. 2006;8(9-10):1791-806.

Payne JW, et al. Conformer profiles and biological activities of peptides. Curr Org Chem. 2002, 6: 1221-46.

Pieper GM, et al. Protective mechanisms of a metalloporphyrinic peroxynitrite decomposition catalyst . . . J Pharmacol Exp Ther. Jul. 2005;314(1):53-60.

Porter EA, et al. Mimicry of host-defense peptides by unnatural oligomers: antimicrobial beta-peptides. J Am Chem Soc. Jun. 26, 2002;124(25):7324-30.

Raguse TL, et al. Structure-activity studies of 14-helical antimicrobial beta-peptides: probing the relationship between conformational stability . . . J Am Chem Soc. Oct. 30, 2002;124(43):12774-85.

Samuni A, Mitchell JB, DeGraff W, Krishna CM, Samuni U, Russo A. Nitroxide SOD-mimics: modes of action. Free Radic Res Commun. 1991;12-13 Pt 1:187-94.

Scaffidi P, Misteli T, Bianchi ME. Release of chromatin protein HMGB1 by necrotic cells triggers inflammation. Nature. Jul. 11, 2002;418(6894):191-5.

Scharte M, Han X, Bertges DJ, Fink MP, Delude RL. Cytokines induce HIF-1 DNA binding and the expression of HIF-1-dependent genes in cultured rat enterocytes. Am J Physiol Gastrointest Liver Physiol. Mar. 2003; 284(3):G373-84.

Schnackenberg CG, Wilcox CS. Two-week administration of tempol attenuates both hypertension and renal excretion of 8-Iso prostaglandin f2alpha. Hypertension. Jan. 1999;33(1 Pt 2):424-8.

Sheu SS, Nauduri D, Anders MW. Targeting antioxidants to mitochondria: a new therapeutic direction. Biochim Biophys Acta. Feb. 2006;1762(2):256-65. Epub Nov. 8, 2005.

Shidoji Y, et al. Loss of molecular interaction between cytochrome c and cardiolipin due to lipid peroxidation. Biochem Biophys Res Commun. Oct. 22, 1999;264(2):343-7.

Sholtz KF, Solovjena NA, Kotelnikova AV, Snezhkova LG, Miroshnikov AI. Effect of gramicidin S and its derivatives on the mitochondrial membrane. FEBS Lett. Oct. 15, 1975;58(1):141-4.

Szeto HH. Mitochondria-targeted peptide antioxidants: novel neuroprotective agents. AAPS J. Aug. 18, 2006;8(3):E521-31.

Tamaki M, et al. CD spectra and cyclization of linear pentapeptides as gramicidin S precursors with a benzyloxycarbonyl group on the side chain . . . Bull Chem Soc Jpn 1993 66(10): 3113-15.

Thiemermann C. Membrane-permeable radical scavengers (tempol) for shock, ischemia-reperfusion injury, and inflammation. Crit Care Med. Jan. 2003;31(1 Suppl):S76-84.

Tuominen EK, et al. Phospholipid-cytochrome c interaction: evidence for the extended lipid anchorage. J Biol Chem. Mar. 15, 2002;277(11):8822-6.

Wade D, et al. Antibiotic properties of novel synthetic temporin A analogs and a cecropin A-temporin A hybrid peptide. Protein Pept Lett. Dec. 2002;9(6):533-43.

Wattanasirichaigoon S, et al. Effect of mesenteric ischemia and reperfusion or hemorrhagic shock on intestinal mucosal permeability and ATP content in rats. Shock. Aug. 1999;12(2):127-33.

Wipf P, et al. Imine Additions of Internal Alkynes for the Synthesis of Trisubstituted (E)-Alkene and Cyclopropane Peptide Isosteres. Adv. Synth. Cat. Oct. 2005;347(11-13):1605-13.

Wipf P, et al. Methyl- and (Trifluoromethyl)alkene Peptide Isosteres: Synthesis and Evaluation of Their Potential as beta-Turn Promoters and Peptide Mimetics. J Org Chem. Sep. 4, 1998;63(18):6088-6089.

Wipf P, et al. Synthesis of chemoreversible prodrugs of ara-C with variable time-release profiles. Biological evaluation of their apoptotic activity. Bioorg Med Chem. Oct. 1996;4(10):1585-96.

Wipf P, Xiao J, Jiang J, Belikova NA, Tyurin VA, Fink MP, Kagan VE. Mitochondrial targeting of selective electron scavengers: synthesis and biological analysis of hemigramicidin-TEMPO conjugates. J Am Chem Soc. Sep. 14, 2005;127(36):12460-1.

Wipf P, Xiao J. Convergent approach to ($E$)-alkene and cyclopropane peptide isosteres. Org Lett. Jan. 6, 2005;7(1):103-6.

Wood PL, et al. Neurotoxicity of reactive aldehydes: the concept of "aldehyde load" as demonstrated by neuroprotection with hydroxylamines. Brain Res. Jun. 20, 2006;1095(1):190-9.

Xiao J, et al. Electrostatic versus steric effects in peptidomimicry: synthesis and secondary structure analysis of gramicidin S analogues with (E)-alkene peptide isosteres. J Am Chem Soc. Apr. 27, 2005;127(16):5742-3.

Yamamoto S, et al R. Anti-tumor promoting action of phthalic acid mono-n-butyl ester cupric salt, a biomimetic superoxide dismutase. Carcinogenesis. May 1990;11(5):749-54.

Yang R, et al. Ethyl pyruvate modulates inflammatory gene expression in mice subjected to hemorrhagic shock. Am J Physiol Gastrointest Liver Physiol. Jul. 2002;283(1):G212-21.

Zhao K et al. Cell-permeable peptide antioxidants targeted to inner mitochondrial membrane inhibit mitochondrial swelling, oxidative cell death, and reperfusion injury. J Biol Chem. Aug. 13, 2004;279(33):34682-90.

* cited by examiner

XJB-5-208

XJB-5-131

USE OF MITOCHONDRIA-TARGETED ELECTRON SCAVENGERS AS ANTI-INFLAMMATORY AGENTS

CROSS-REFERENCE TO RELATED APPLICATIONS

This application claims the benefit under 35 U.S.C. §119(e) to U.S. Provisional Patent Application No. 60/954,661, filed on Aug. 8, 2007, which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Contract No. W81XWH-05-2-0026 awarded by Defense Advanced Research Projects Administration and by the terms of Grant No. GM067082 awarded by the U.S. Public Health Service National Institutes of Health.

Provided herein are methods for using mitochondria-targeted electron scavengers as an anti-inflammatory agent. The mitochondria-targeted electron scavenger can be used to treat medical conditions associated with acute or chronic inflammation.

Reactive oxygen species ("ROS") and reactive nitrogen species ("RNS") are two major types of compounds, including as a class free radicals and free radical derivatives, with important physiological functions in organisms. ROS and RNS include not only radicals, but other related non-radical species that are formed during intracellular oxidation processes. ROS include radical species, such as superoxide radical anion ($O_2^-$.) and hydroxyl radical (.OH); and related non-radical species, such as peroxide (ROOR), hydrogen peroxide ($H_2O_2$), singlet oxygen ($^1O_2$), and peroxynitrite ($ONOO^-$). RNS include radical species, such as nitric oxide (.NO); and related non-radical species, such as nitrosonium cation ($NO^+$), nitroxyl anion ($NO^-$), and peroxynitrite ($ONOO^-$). These free radicals and related species participate in the regulation of signal transduction from membrane receptors, immunological and inflammatory responses, smooth muscle relaxation, redox homeostasis, apoptosis, and vascular tone, among others. Proper regulation of ROS and RNS provides protection against oxidative stress and provides important mediators in cellular processes. However, excessive production or improper clearance of ROS and RNS can result in damage to cellular constituents, such as proteins, DNA, and membrane lipids; dysfunction of intracellular signaling cascades; cytotoxicity; and enzyme inactivation. Free radicals have been implicated as being important in the pathogenesis in a wide range of diseases and pathological processes, including various forms of cancer, type 2 diabetes mellitus, atherosclerosis, chronic inflammatory conditions, ischemia/reperfusion injury, sepsis and some neurodegenerative diseases (Dröge W. Free radicals in the physiological control of cell function. Physiol Rev 2002, 82:47-95).

Reactive oxygen species ("ROS") are intermediates formed as a result of the partial reduction of molecular oxygen (dioxygen; $O_2$). Some important ROS in biological systems include superoxide radical anion ($O_2^-$.), hydrogen peroxide ($H_2O_2$), and hydroxyl radical (.OH). Nonradical reactive oxygen species include singlet oxygen ($^1O_2$), hydrogen peroxide ($H_2O_2$), and peroxynitrite ($ONOO^-$). Numerous enzymatic processes, such as the reactions catalyzed by xanthine oxidase, nicotinamide adenine dinucleotide phosphate (NADPH) oxidase isoforms and cyclooxygenase isoforms, lead to the formation of ROS (Fink M P. Reactive oxygen species as mediators of organ dysfunction caused by sepsis, acute respiratory distress syndrome, or hemorrhagic shock: potential benefits of resuscitation with Ringer's ethyl pyruvate solution. Curr Opin Clin Nutr Metab Care 2002, 5:167-174).

Reactive nitrogen species ("RNS") are intermediates formed as a result of oxidation of L-arginine. This oxidation process is catalyzed by nitric oxide synthase (NOS) isoforms and results in the formation of nitric oxide (.NO). There are three NOS isoforms: neuronal NOS (nNOS), endothelial NOS (eNOS), and inducible NOS (iNOS). These isoforms are expressed in various subcellular locations and tissues, where non-limiting examples include cardiac myocytes, glial cells, skeletal cells, neutrophils, vascular smooth muscle cells, and platelets. Nitric oxide can be converted into other nonradical RNS, such as nitrosonium cation ($NO^+$), nitroxyl anion ($NO^-$), and peroxynitrite ($ONOO^-$, a toxic compound formed from a reaction between nitric oxide and superoxide anion).

Reactive oxygen species ("ROS") and reactive nitrogen species ("RNS") could play critical roles as mediators in a number of different intracellular signaling cascades, including inflammatory processes (Dröge W, Physiol Rev 2002, 82:47-95). Abnormalities associated with inflammation include chronic inflammation and acute inflammation, which can result in further physiological and pathophysiological conditions, such as autoimmune diseases. In particular, ROS have been implicated in the regulation of signaling mediated by the pro-inflammatory transcription factors, NF-κB (Pantano C, Reynaert N L, van der Vliet A et al. Redox-sensitive kinases of the nuclear factor-kappaB signaling pathway. Antioxid Redox Signal 2006, 8:1791-1806; Gloire G, Legrand-Poels S, Piette J. NF-kappaB activation by reactive oxygen species: fifteen years later. Biochem Pharmacol 2006, 72:1493-1505) and activator protein (AP)-1 (Liu H, Colavitti R, Rovira I I et al. Redox-dependent transcriptional regulation. Circ Res 2005, 97:967-974; Lin S J, Shyue S K, Hung Y Y et al. Superoxide dismutase inhibits the expression of vascular cell adhesion molecule-1 and intracellular cell adhesion molecule-1 induced by tumor necrosis factor-alpha in human endothelial cells through the JNK/p38 pathways. Arterioscler Thromb Vasc Biol 2005, 25:334-340). Redox-dependent signaling mechanisms also have been implicated in the activation of pro-inflammatory mitogen-activated protein kinases (MAPK), including p38 and JNK (Nagai H, Noguchi T, Takeda K et al. Pathophysiological roles of ASK1-MAP kinase signaling pathways. J Biochem Mol Biol 2007, 40:1-6). Expression of nitric oxide synthase isoforms have been associated with inflammation, where induction of inducible nitric oxide synthase (iNOS) can be initiated by liposaccharide (LPS), endotoxin, or inflammatory cytokines, such as IFN-γ, TNF-αc, and IL-1 (Guzik T J, Korbut R, Adamek-Guxik T. Nitric oxide and superoxide in inflammation and immune regulation. J Physiol Pharmacol 2003, 54(4):469-87).

SUMMARY

It has unexpectedly been found that antioxidants that target mitochondria have a significant impact on inflammation and find use as anti-inflammatory agents. Therefore, provided herein are methods of treating inflammation in a patient and related compositions and kits.

Therefore, a method is provided of treating inflammation in a patient comprising administering to the patient a mitochondria-targeted electron scavenger comprising a free radical-scavenging group covalently linked to a mitochondria-targeting group, for example by an ester or amide linkage. The mitochondria-targeted electron scavenger is administered in an amount effective to reduce inflammation in the patient. In one non-limiting embodiment, the mitochondria-targeting group is a hemigramicidin or a stereoisomer or isostere thereof, or a pharmaceutically acceptable salt thereof.

The mitochondria-targeting group may be acylated. The mitochondria-targeting group may comprise one or more N-acylated amino acids within the hemigramicidin moiety, wherein the amino acid is acylated with one or more of the following acylating agents: aryloxycarbonyl agents, including benzyloxycarbonyl (Cbz) and fluorene-9-methyloxycarbonyl (FMOC) agents; and alkyloxycarbonyl agents, including tert-butoxycarbonyl (Boc), methoxycarbonyl, and trichloroethoxycarbonyl agents. For example and without limitation, the amino acid Leu is acylated with a tert-butoxycarbonyl (Boc) agent, such that the acyl group is Boc and the N-acylated amino acid is N-Boc-Leu.

In certain non-limiting examples, the N-acylated amino acid is N-Boc-Leu and/or Orn(Cbz). In others, the amino acid is acylated with one or more of the following acylating agents: aryloxycarbonyl agents, including benzyloxycarbonyl (Cbz) and fluorene-9-methyloxycarbonyl (FMOC) agents; and alkyloxycarbonyl agents, including tert-butoxycarbonyl (Boc), methoxycarbonyl, and trichloroethoxycarbonyl agents.

In one non-limiting embodiment, the hemigramicidin has the amino acid sequence Leu-$^D$Phe-Pro-Val-Orn that is optionally acylated. In another, the mitochondria-targeting group is chosen from one of Leu-R-$^D$Phe-Pro-Val-Orn and Leu-R-$^D$Phe, in which neither, one or both of the Orn and Leu, independently, are N-acylated, and R is the linkage between the Leu and $^D$Phe residues and is one of cyclopropane (i.e., △ ), -(E)-CH=CH—, -(E)-CH=C(CH$_3$)—, and —C(=O)NH— (amide or peptide bond), or an isostere, stereoisomer or pharmaceutically-acceptable salt thereof. For example and without limitation, the mitochondria-targeting group comprises a β-turn motif, such as a peptide bond, an alkene bond, an (E)-alkene bond or a cyclopropane ring. In certain non-limiting examples, the mitochondria-targeting group comprises two or more amino acids from the hemigramicidin moiety Leu-$^D$Phe-Pro-Val-Orn, such as Leu-$^D$Phe, N-Boc-Leu-[(E)-CH=CH]-$^D$Phe, Leu-$^D$Phe-Pro-Val-Orn, N-Boc-Leu-[(E)-CH=CH]-$^D$Phe-Pro-Val-Orn(Cbz). In other non-limiting examples, the mitochondria-targeted electron scavenger comprises:

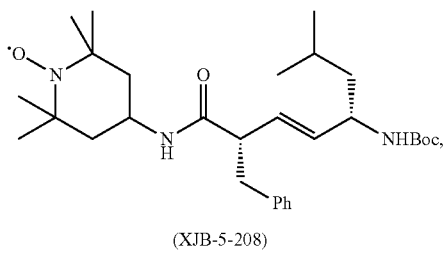

(XJB-5-208)

or a pharmaceutically acceptable salt thereof, or

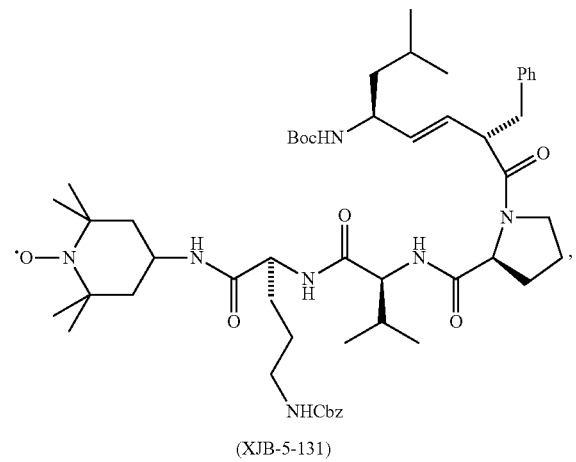

(XJB-5-131)

or a pharmaceutically acceptable salt thereof.

In another non-limiting embodiment, the free radical-scavenging group comprises a nitroxide group, for example and without limitation, the free radical-scavenging group comprises one of 2,2,6,6-tetramethylpiperidine-N-oxyl, 4-hydroxy-2,2,6,6-tetramethylpiperidine-N-oxyl, and 4-amino-2,2,6,6-tetramethylpiperidine-N-oxyl.

The inflammation may be chronic or acute. Non-limiting examples of inflammatory conditions include one or more of an infection, a wound, an autoimmune disease, and endotoxin-induced inflammation, for example and without limitation, one or more of sepsis, septic shock, an autoimmune disease, rheumatoid arthritis, inflammatory bowel disease, colitis, ulcerative colitis, Crohn's disease, ileitis, endotoxin-induced inflammation, aberrant wound healing, diabetic foot ulcers, multiple sclerosis, psoriasis, congestive heart failure, and asthma. The patient may be human. The mitochondria-targeted electron scavenger may be administered to the patient parenterally or orally, or by any useful route for any useful time period effective to treat the inflammation.

Also provided is a composition for treating inflammation in a patient comprising a mitochondria-targeted electron scavenger in an amount effective to treat the inflammation in a pharmaceutically acceptable carrier. A kit also is provided comprising one or more unit doses for treating inflammation in a patient, the unit doses comprising a mitochondria-targeted electron scavenger in an amount effective to treat the inflammation in a pharmaceutically acceptable carrier in a container.

BRIEF DESCRIPTION OF THE DRAWINGS

FIG. 2A shows the effect of graded concentrations of XJB-5-131 on nitric oxide secretion, where results are means±SEM (n=4 per condition). FIG. 2B shows the effect of graded concentrations of XJB-5-208 on nitric oxide secretion, where results are means±SEM (n=3 per condition). Effects of DMSO (dimethyl sulfoxide)

are shown as a control. Results depicted are representative of an experiment, which was repeated three times with similar findings. * indicates p<0.05 versus cells treated only with LPS.

Figure 3A:
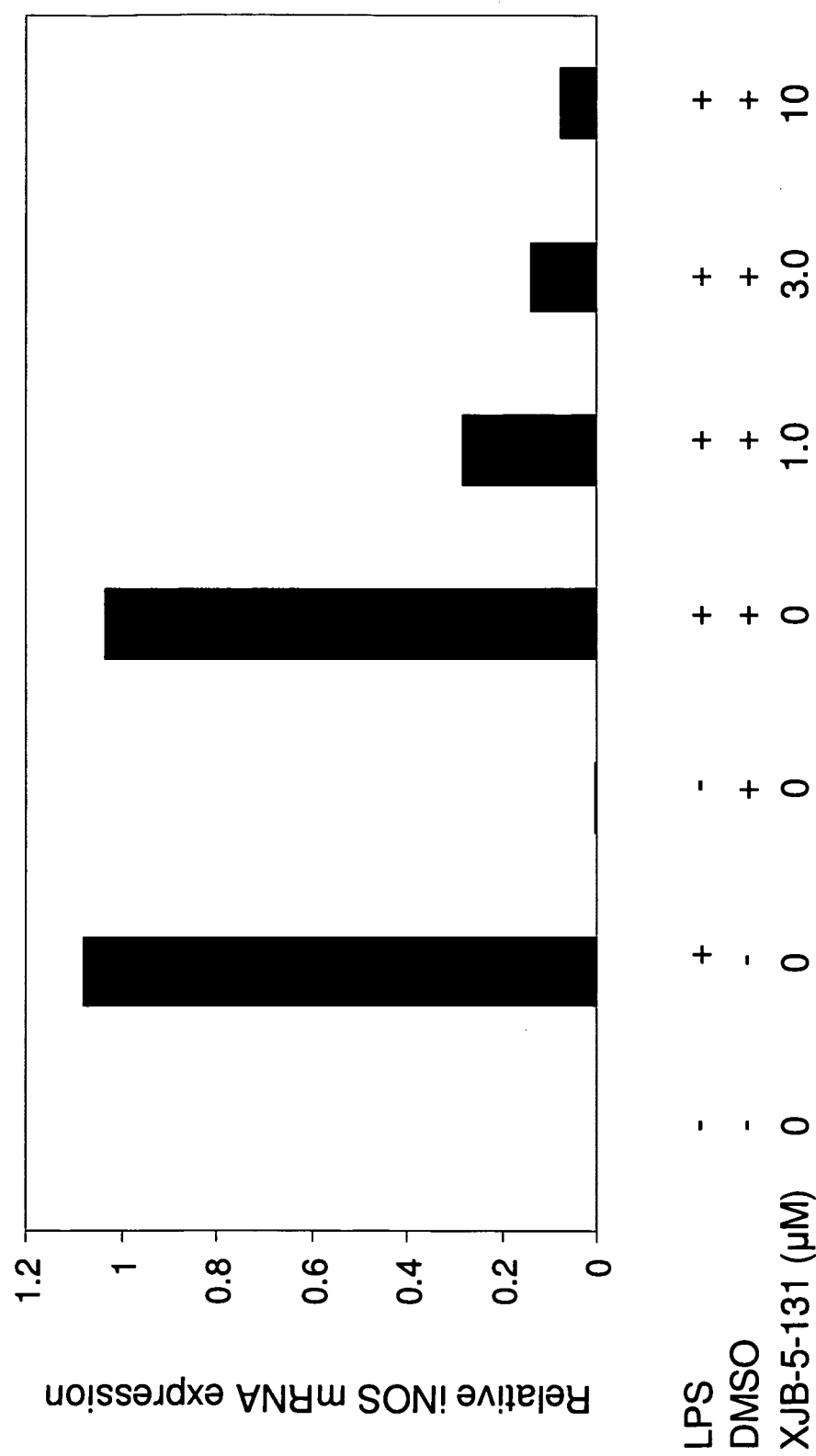
Figure 3B:
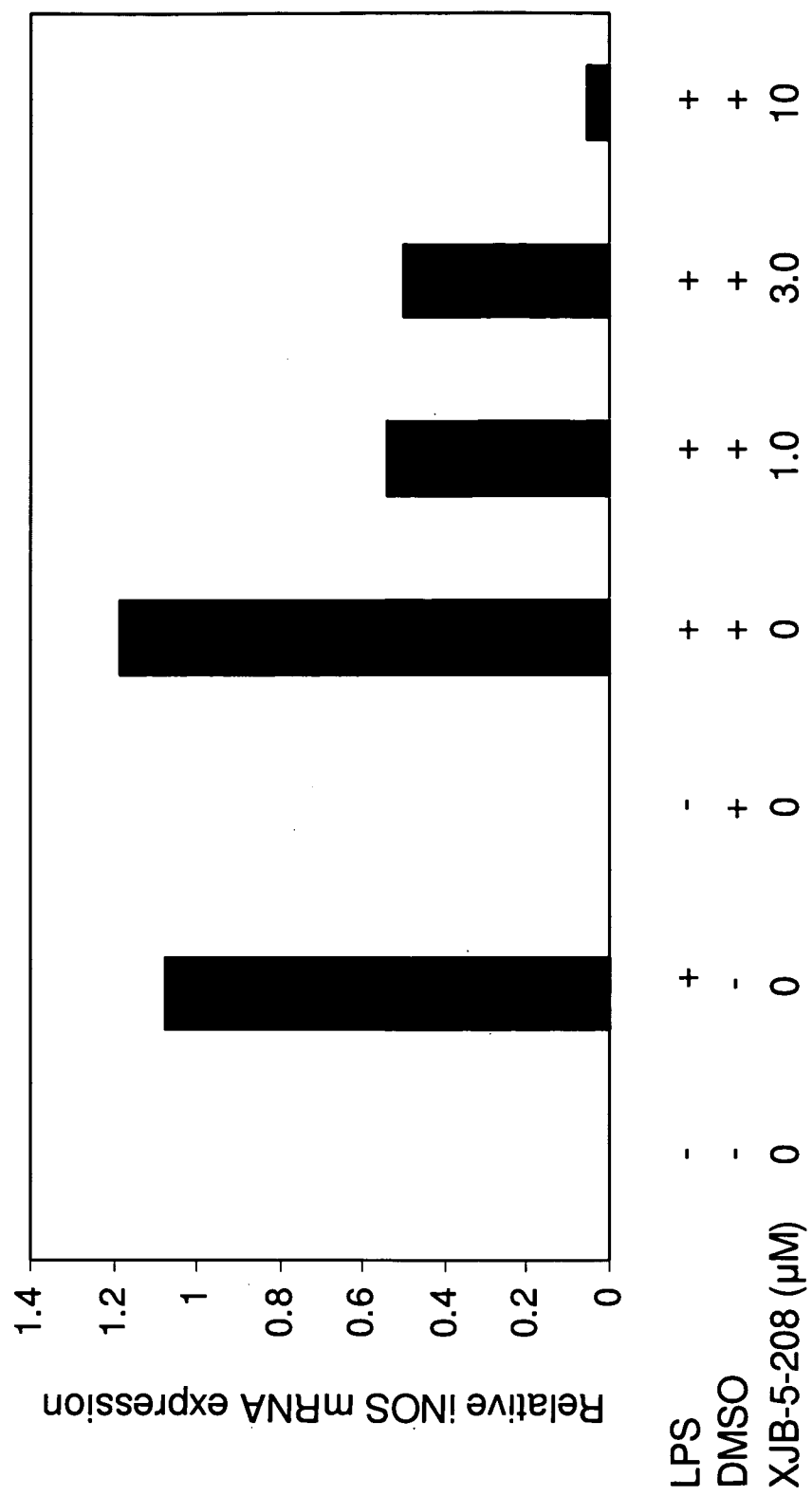

FIGS. 3A-3B are graphs showing expression of inducible nitric oxide synthase (iNOS) mRNA in lipopolysaccharide (LPS)-stimulated RAW 264.7 cells. FIG. 3A shows the effect of graded concentrations of XJB-5-131 on iNOS mRNA expression. FIG. 3B shows the effect of graded concentrations of XJB-5-208 on iNOS mRNA expression. Effects of DMSO are shown as a control. Results depicted are representative of an experiment, which was repeated three times with similar findings.

Figure 4A:
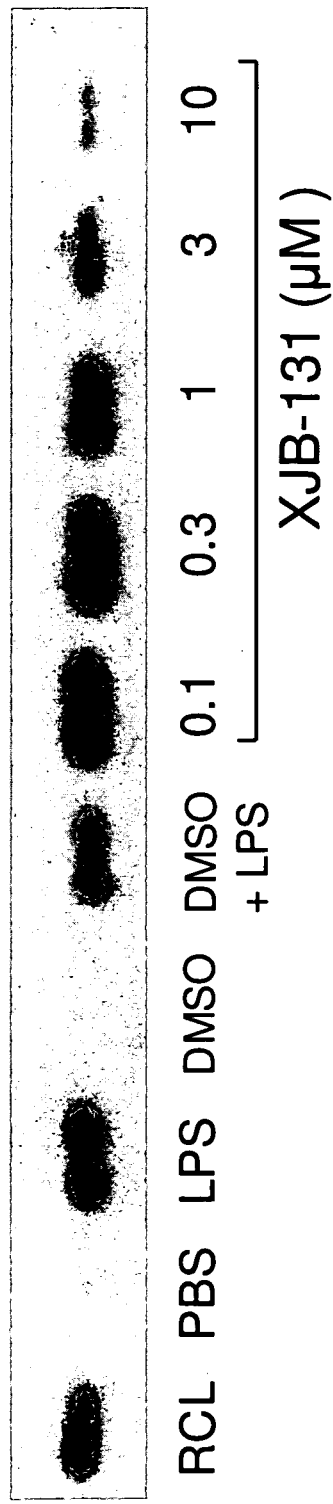
Figure 4B:
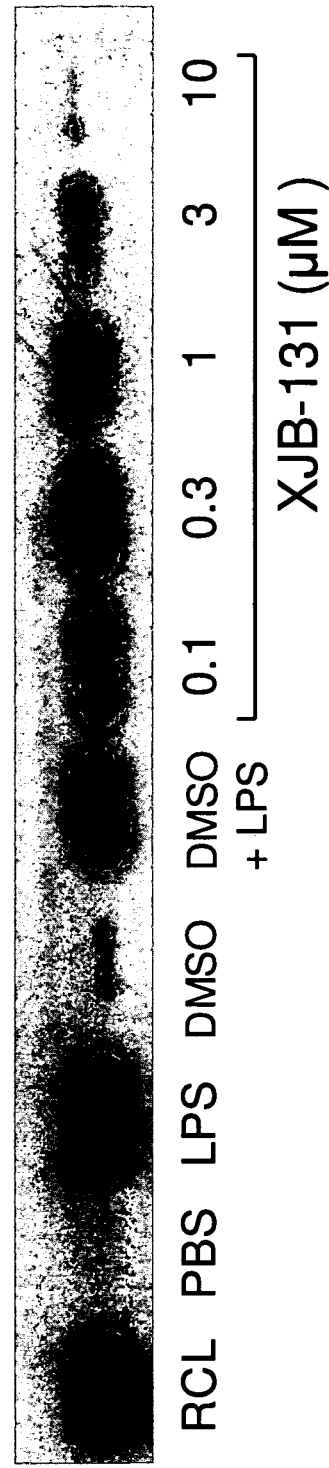

FIGS. 4A-4B are western blots of HMGB 1 secretion by lipopolysaccharide (LPS)-stimulated RAW 264.7 cells. FIG. 4A shows the effect of graded concentrations of XJB-5-131 incubated for 48 hours with the cells. FIG. 4B shows the effect of graded concentrations of XJB-5-131 incubated for 72 hours with the cells. "RCL" refers to raw cell lysate and was used as a positive control. Results depicted are representative of an experiment, which was repeated four times with similar findings.

Figure 5:
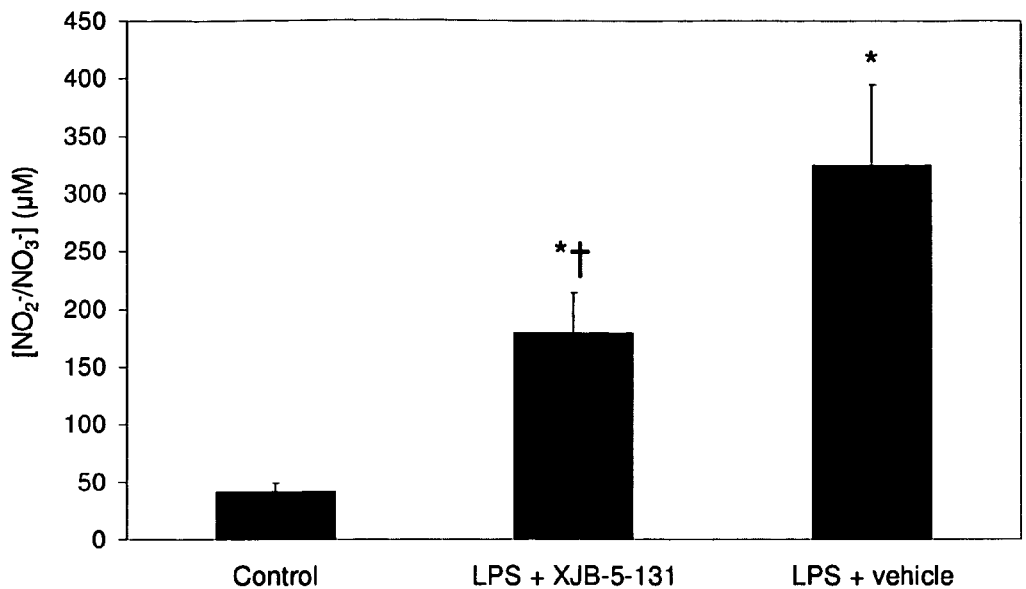

FIG. 5 is a graph showing nitric oxide levels within blood plasma from C57B1/6 mice challenged with lipopolysaccharide (LPS). Nitric oxide secretion was measured by detecting nitrite and nitrate ($NO_2^-/NO_3^-$) within blood plasma. FIG. 5 shows the effect of pretreatment with XJB-5-131 on nitric oxide levels in vivo. "Vehicle" refers to a saline solution. Data also were obtained from Control mice (n=18), which were treated with neither LPS nor XJB-5-131. Results are means±SEM. * indicates p<0.05 versus Control; t indicates p<0.05 versus vehicle-treated LPS-challenged mice.

Figure 6:
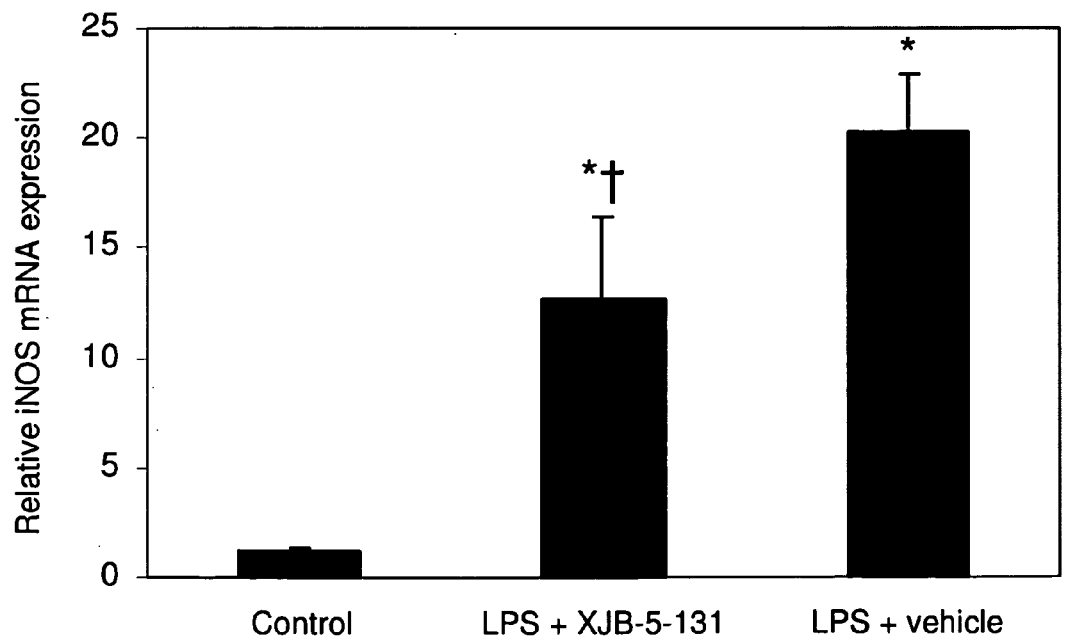

FIG. 6 is a graph showing expression of iNOS mRNA within hepatic tissue from C57B1/6 mice challenged with lipopolysaccharide (LPS). FIG. 6 shows the effect of pretreatment with XJB-5-131 on iNOS mRNA levels in vivo. "Vehicle" refers to a 67:33 (v/v) mixture of DMSO and saline solution. Data also were obtained from Control mice (n=18), which were treated with neither LPS nor XJB-5-131. Results are means±SEM. * indicates p<0.05 versus Control; t indicates p<0.05 versus vehicle-treated LPS-challenged mice.

DETAILED DESCRIPTION

Provided herein are methods, compositions and kits for scavenging reactive oxygen species ("ROS") and reactive nitrogen species ("RNS") that are present within the mitochondria to treat a patient for medical conditions associated with inflammation. Unexpectedly, by use of these methods, compositions and kits, inflammation can be effectively treated. The methods, compositions and kits employ a mitochondria-targeted electron scavenger for scavenging excess ROS and RNS produced by naturally-occurring enzymes such as superoxide dismutase and catalase, among others. The mitochondria-targeted electron scavenger comprises an electron-scavenging group (or moiety) attached to a mitochondria-targeting group. In one non-limiting embodiment, the mitochondria-targeted electron scavenger comprises a free radical-scavenging group covalently linked to a mitochondria-targeting group derived from the hemigramicidin moiety Leu-$^D$Phe-Pro-Val-Orn (e.g.:

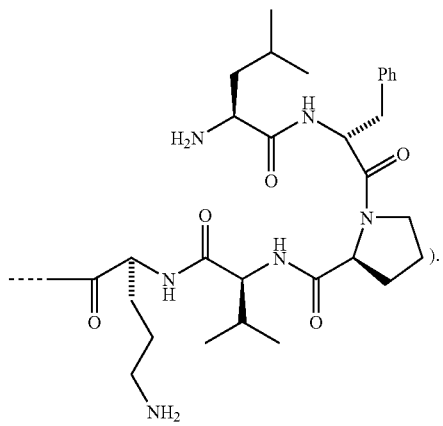

As used herein, the term "patient" refers to members of the animal kingdom including but not limited to human beings.

As used herein, the terms "free radical" and "free radical derivatives" both refer to molecules that are considered to be ROS and/or RNS. ROS include both radical and nonradical species formed as a result of the partial reduction of molecular oxygen (dioxygen; $O_2$). Non-limiting examples of ROS include superoxide radical anion ($O_2^-$.), hydrogen peroxide ($H_2O_2$), hydroxyl radical (.OH), singlet oxygen ($^1O_2$), and peroxynitrite ($ONOO^-$). RNS include both radical and non-radical species formed as a result of the oxidation of L-arginine. Non-limiting examples of RNS include nitric oxide (.NO), nitrosonium cation ($NO^+$), nitroxyl anion ($NO^-$), and peroxynitrite ($ONOO^-$).

As used herein, a "mitochondria-targeted electron scavenger" is a compound comprising a free radical-scavenging group covalently linked to a mitochondria-targeting group. In one non-limiting example, the mitochondria-targeted electron scavenger is XJB-5-131. In another non-limiting example, the mitochondria-targeted electron scavenger is XJB-5-208.

Medical conditions associated with inflammation include those that result in abnormal regulation or up-regulation of the immune response, such as with chronic inflammation or acute inflammation. Non-limiting examples of medical conditions associated with inflammation include those that result from an infection, such as sepsis; an autoimmune disease, such as rheumatoid arthritis; and inflammatory bowel disease, including colitis, Crohn's disease, ileitis, and endotoxin-induced inflammation. Wound healing comprises an inflammatory component that can go awry, thus necessitating treatment of inflammation, for example in chronic wound conditions, such as diabetic foot ulcers. Medical conditions associated with inflammation also include those conditions, such as rheumatoid arthritis, Crohn's disease, ulcerative colitis, multiple sclerosis, psoriasis, congestive heart failure, asthma, sepsis, septic shock, and conditions that are mediated by pro-inflammatory cytokines and transcription factors, such as, for example and without limitation, high mobility group box-1 (HMGB 1); nuclear factor-κB (NF-κB), activator protein-1 (AP-1); mitogen-activated protein kinases (MAPK), such as p38 and JNK; IFN-γ; TNF-α; and IL-1. Medical conditions associated with inflammation also include those that result in the up-regulation of pro-inflammatory markers, such as, for example and without limitation, the up-regulation of iNOS to form increased NO or increased iNOS mRNA expression in conditions such as ulcerative colitis, cardiogenic shock, septic shock, and asthma. Another non-limiting example includes a condition, such as rheumatoid arthritis, hemorrhagic shock, sepsis, septic and shock, that results in the up-regulation of pro-inflammatory cytokines and extracellular secretion of a cytokine-like marker, HMGB1.

"Treatment" of a medical condition associated with inflammation or "treatment of inflammation" means administration to a patient by any suitable route and dosage regimen of a mitochondria-targeted electron scavenger with the object of ameliorating (alleviating, reducing and/or normalizing) any symptom and/or indicia associated with the medical condition, including, without limitation, any testable parameter, whether or not subjective, such as, without limitation, pain levels, or objective, such as, without limitation, pro-inflammatory cytokine levels or other biomarkers in blood sample of a patient, or lesion size. Likewise "treating" such a medical condition or inflammation may result in amelioration of any symptom and/or indicia associated with the medical condition or inflammation in a patient.

By "reducing" inflammation within a patient, it is meant that the patient's medical condition has reached any exemplary endpoint useful in the art of medical diagnosis that indicates ameliorating (alleviating, reducing and/or normalizing) inflammation. A non-limiting exemplary endpoint includes reduction of the patient's symptoms associated with an inflammatory disease, where such symptoms include pain, swelling, fever, and/or fatigue. Another non-limiting exemplary endpoint includes reduction of pro-inflammatory biomarkers within a biological sample from the patient, where such biomarkers include cytokines, nitrites, and/or interleukins.

Reduction of inflammation can be assessed by any method that can be used when diagnosing or treating a medical condition associated with inflammation. For example, the reduction of inflammation can be correlated to a reduction of symptoms and pain associated with a chronic inflammatory disease. In another example, the reduction of inflammation can be correlated to a reduction of pro-inflammatory cytokines or biomarkers within a blood sample from the patient. In another non-limiting example, the reduction of inflammation can be correlated to a reduction of bacteria within a biological sample from the patient.

The conditions for administration of the mitochondria-targeted electron scavenger, and thus the dosage form used to deliver the scavenger may vary depending on a number of variables, including, without limitation, the medical condition sought to be treated and/or the age, weight or medical condition of the patient. For example and without limitation, conditions associated with acute inflammation may be treated by intravenous administration of a mitochondria-targeted electron scavenger to the patient. In another non-limiting example, conditions associated with chronic inflammation may be treated by oral administration of the mitochondria-targeted electron scavenger to the patient. In yet another non-limiting example, the condition associated with inflammation may be treated by co-administering a mitochondria-targeted electron scavenger with a second mitochondria-targeted electron scavenger.

Administration of the mitochondria-targeted electron scavenger to a patient can further comprise mixing the mitochondria-targeted electron scavenger with a pharmaceutically acceptable carrier. A "carrier" includes as a class any compound or composition useful in facilitating storage, stability, administration, cell targeting and/or delivery of the mitochondria-targeted electron scavenger, including, without limitation, suitable vehicles, diluents, solvents, excipients, pH modifiers, salts, colorants, flavorings, rheology modifiers, lubricants, coatings, fillers, antifoaming agents, erodeable polymers, hydrogels, surfactants, emulsifiers, adjuvants, preservatives, phospholipids, fatty acids, mono-, di- and tri-glycerides and derivates thereof, waxes, oils and water. In one embodiment, the mitochondria-targeted electron scavenger is suspended in water (USP) for delivery in vivo. Pharmaceutically acceptable salts, buffers or buffer systems, including, without limitation, saline, phosphate buffer or phosphate buffered saline (PBS) may be included in the dosage form. Vehicles having the ability to facilitate delivery of nucleic acids and/or nucleic acid analogs to a cell in vivo, such as liposomes, may be utilized to facilitate delivery of the decoy to the target cells. One non-limiting example of such a vehicle is a cationic liposome system, for example and without limitation as shown in U.S. Pat. Nos. 6,656,498, 6,696,038 and 6,749,863.

The mitochondria-targeted electron scavenger may be administered in any amount effective to treat a medical condition associated with inflammation. Non-limiting examples of dosage ranges for the mitochondria-targeted electron scavenger include from about 1 to about 100 µmoles/Kg (micromoles per kilogram) per dose and any increment therebetween, such as from 1 to about 10 µmoles/Kg and from about 10 to about 100 µmoles/Kg for each dose, including increments therebetween. Doses can also be delivered to the patient in any effective regimen, for example and without limitation, every other day, daily, every 1, 2, 3, 4, 6, 8 or 12 hours or continuously. For example, and without limitation, in the case of XJB-5-131 a useful dose of 1-100 µmoles/Kg may be administered every 12 hours. More or less drug product may be found to be effective in a given patient, and would be administered in a dosage form. The amount administered to a patient will vary depending upon a number of parameters, including: the specific activity of the active ingredient when in a patient's blood, the bioavailability of the active ingredient as a function of the route of administration, and the patient's age, weight, sex, health, genetics, etc.

Pharmaceutically acceptable salt forms of the compounds described herein may be prepared by conventional methods known in the pharmaceutical arts. For example and without limitation, where the compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Thus, non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Compounds comprising basic nitrogen-containing groups may be quaternized with such agents as $C_1$-$C_4$ alkyl halides, such as methyl, ethyl, iso-propyl and tert-butyl chlorides, bromides and iodides; $C_1$-$C_4$ alkyl sulfate such as dimethyl, diethyl and diamyl sulfates; $C_{10}$-$C_{18}$ alkyl halides, such as decyl, dodecyl, lauryl, myristyl and stearyl chlorides, bromides and iodides; and aryl-$C_1$-$C_4$ alkyl halides, such as benzyl chloride and phenethyl bromide. Such salts permit the preparation of both water-soluble and oil-soluble compounds.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient comprising a salt form of a mitochondria-targeted electron scavenger. The salt form preferably confers to the scavenger improved and/or desirable pharmacokinetic/pharmodynamic properties as compared to the free base form of the scavenger.

As a group, "stereoisomers" of any described compound, such as a described mitochondria-targeted electron scavenger, include enantiomers, diastereomers, cis and trans (E and Z) isomers and conformers thereof. As a group, stereoisomers of a given active agent can, and often do have similar safety and efficacy as the active agent.

In another non-limiting embodiment, mitochondria-targeted electron scavenger may be co-administered with any particular class of compound to treat inflammation, such as, without limitation: non-steroidal anti-inflammatory drugs ("NSAIDS"), including naproxen, ibuprofen, diclofenac, aspirin, and celecoxib; salicylates, such as salicylic acid and melsalamine; corticosteroids, such as hydrocortisone, prednisone, methylprednisone, dexamethasone; anti-TNF antibodies, such as entanercept (Enbrel®), infliximab (Remicade®), and adalimumab (Humira®); organogold compounds; D-penicillamine (Plaquinyl®); and anti-metabolic agents, such as methotrexate. The choice of agent(s) to be co-administered with the scavenger typically depends on a number of factors, such as, the nature of the patient's inflammatory condition and the severity of the condition in a patient. A patient suffering from inflammatory bowel disease likely will be treated differently than a patient suffering from Rheumatoid arthritis, sepsis or trauma.

By "not toxic" or "non-toxic" it is meant that the mitochondria-targeted electron scavenger, and normal in vivo degradation products thereof, do not cause substantial harm to cells, tissues, organs or patients, and are non-carcinogenic within useful, practical, and/or acceptable tolerances. In one example, the mitochondria-targeted electron scavenger is non-toxic because it is "safe" according to applicable regulatory standards of a jurisdiction, such as those of and pertaining to the United States Food and Drug administration or its equivalent in other jurisdiction(s). For example, the mitochondria-targeted electron scavenger when used to treat cells may not substantially adversely affect the viability, growth, and number of cells. In another non-limiting example, the mitochondria-targeted electron scavenger may affect regulatory processes within the mitochondria but does not substantially adversely affect cellular processes within other organelles or compartments of a cell, such as the nucleus. The potential toxicity of the mitochondria-targeted electron scavenger can be minimized in many ways. For example and without limitation, the dosage amount of the mitochondria-targeted electron scavenger used for treatment can be decreased or dosage form of the mitochondria-targeted electron scavenger used for treatment can be altered. According to one non-limiting embodiment, the mitochondria-targeting group of the mitochondria-targeted electron scavenger or portions thereof can be acylated to reduce cytotoxicity. For example, the amino functions of Leu and Orn are acylated (Jelokhani-Niaraki M, Kondejewski L H, Farmer S W et al. Diastereoisomeric analogues of gramicidin S: structure, biological activity and interaction with lipid bilayers. Biochem J 2000, 349 Pt 3:747-755).

As used herein, the term "free radical-scavenging group" refers to a chemical moiety comprising a chemical group that can be used to scavenge free radicals (also referred to as an electron scavenger). Relevant free radicals include one or more of free radicals present in biological systems, such as a RNS or a ROS. In one embodiment, the chemical moiety comprises a nitroxide group, such as, without limitation, a 2,2,6,6-tetramethylpiperidine-N-oxyl group, where the nitroxide group can be used to scavenge superoxide anions. Non-limiting examples of chemical moieties comprising a stable nitroxide group .O—$NR_2$ include: 2,2,6,6-tetramethylpiperidine-N-oxyl (TEMPO); 4-hydroxy-2,2,6,6-tetramethylpiperidine-N-oxyl (TEMPOL); 4-amino-2,2,6,6-tetramethylpiperidine-N-oxyl (4-AT or 4-$NH_2$-TEMPO); tert-butyl isopropyl phenyl nitroxide; 2,2,5,5-tetramethylpyyridine-N-oxyl (PROXYL); 4,4-dimethyloxazolidine-N-oxyl (DOXYL); and derivatives thereof. As is known to one ordinarily skilled in the art, nitroxide and nitroxide derivatives, including TEMPOL and associated TEMPO derivatives are stable radicals that can withstand biological environments. Therefore, the presence of nitroxide and nitroxide derivatives within the mitochondrial membrane can serve as an effective and efficient electron scavenger of the ROS being produced within the membrane.

Additional non-limiting examples of nitroxides (or —N—O•, —N—OH, N═O containing groups) are provided in Table 1 and Table 2 (from Jiang J, et al. Structural requirements for optimized delivery, inhibition of oxidative stress, and antiapoptotic activity of targeted nitroxides. J Pharmacol Exp Ther. 2007 March; 320(3):1050-60). A person of ordinary skill in the art would be able to conjugate (covalently attach) any of these compounds to the rest of the compound using common linkers and/or conjugation chemistries, such as the chemistries described herein. Table 1 provides a non-limiting excerpt from a list of over 300 identified commercially-available —N—O•, —N—OH or N═O containing compounds that may be useful in preparation of the compounds or compositions described herein. Table 2 provides non-limiting examples of certain other nitroxides. The Log P values were estimated using the online calculator of molecular properties and drug likeness on the Molinspirations Web site (www.molinspiration.com/cgi-bin/properties). TIPNO=tert-butyl isopropyl phenyl nitroxide.

TABLE 1

Commercially-available —N—O•, —N—OH or N═O containing groups

| Structure | Name | CAS No. |
|---|---|---|
| 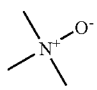 | Trimethylamine N-Oxide | 1184-78-7 |
| 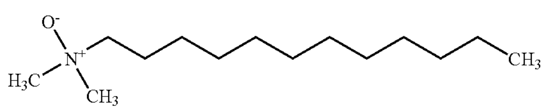 [SMILES: CCCCCCCCCCCC[N+](C)(C)[O-]] | N,N-Dimethyldodecylamine N-Oxide | 1643-20-5<br>70592-80-2 |
| 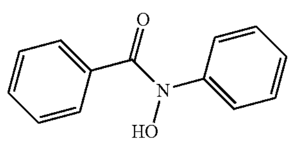 [SMILES: O=C(c1ccccc1)N(O)c1ccccc1] | N-Benzoyl-N-Phenylhydroxylamine | 304-88-1 |
| 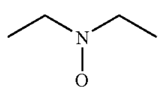 | N,N-Diethylhydroxylamine | 3710-84-7 |
| 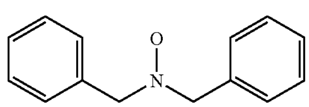 [SMILES: ON(Cc1ccccc1)Cc1ccccc1] | N,N-Dibenzylhydroxylamine | 14165-27-6<br>621-07-8 |
| 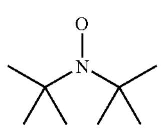 | Di-Tert-Butyl Nitroxide | 2406-25-9 |
| 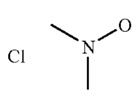 | N,N-Dimethylhydroxylamine Hydrochloride | 16645-06-0 |
| 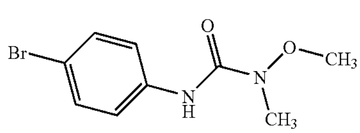 | Metobromuron | 3060-89-7 |
| 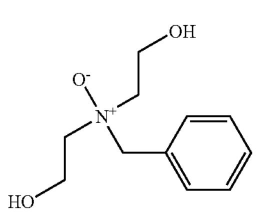 [SMILES: [O-][N+](CCO)(CCO)Cc1ccccc1] | Benzyl-Di-Beta-Hydroxy Ethylamine-N-Oxide |  |

TABLE 1-continued

Commercially-available —N—O•, —N—OH or N=O containing groups

| Structure | Name | CAS No. |
| --- | --- | --- |
| (structure) | Bis(Trifluoromethyl)Nitroxide | 2154-71-4 |
| (structure) | Triethylamine N-Oxide | 2687-45-8 |
| (structure) | Desferrioxamine mesylate salt, | CAS No. 138-14-7 |
| (structure) | N-Methoxy-N-Methylcarbamate | 6919-62-6 |
| (structure) | N,N-Bis(2-Chloro-6-Fluorobenzyl)-N-[(([2,2-Dichloro-1-(1,4-Thiazinan-4-yl+)Ethylidene]amino)Carbonyl)Oxy]Amine | |
| (structure) | Tri-N-Octylamine N-Oxide | 13103-04-3 |
| (structure) | Diethyl (N-Methoxy-N-Methylcarbamoylmethyl) Phosphonate | 124931-12-0 |

TABLE 1-continued

Commercially-available —N—O•, —N—OH or N=O containing groups

| Structure | Name | CAS No. |
|---|---|---|
| 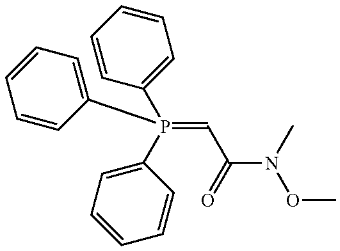 [SMILES: CON(C)C(=O)C=P(c1ccccc1)(c1ccccc1)c1ccccc1] | N-Methoxy-N-Methyl-2-(Triphenylphosphoranylidene)Acetamide | 129986-67-0 |
| 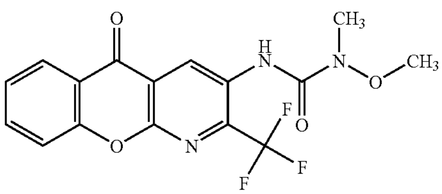 [SMILES: CON(C)C(=O)Nc1cc2c(=O)c3ccccc3oc2nc1C(F)(F)F] | N-Methoxy-N-Methyl-N'-[5-Oxo-2-(Trifluoromethyl)-5h-Chromeno[2,3-B]Pyridi+N-3-Yl]Urea | |
| 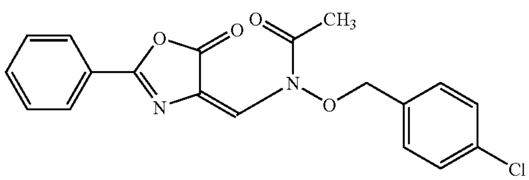 [SMILES: CC(=O)N(/C=C1/N=C(c2ccccc2)OC1=O)OCc1ccc(Cl)cc1] | N-[(4-Chlorobenzyl)Oxy]-N-([5-Oxo-2-Phenyl-1,3-Oxazol-4(5h)-Yliden]Methyl+)Acetamide | |
| 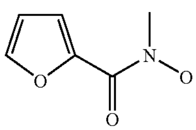 | N-Methylfurohydroxamic Acid | 109531-96-6 |
| 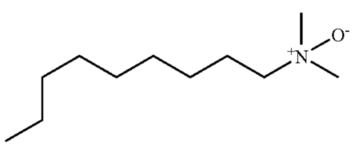 | N,N-Dimethylnonylamine N-Oxide | 2536-13-2 |
| 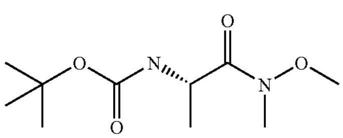 [SMILES: CON(C)C(=O)[C@H](C)NC(=O)OC(C)(C)C] | N-(Tert-Butoxycarbonyl)-L-Alanine N'-Methoxy-N'-Methylamide | 87694-49-3 |
| 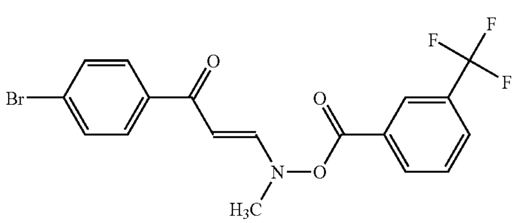 [SMILES: CN(/C=C/C(=O)c1ccc(Br)cc1)OC(=O)c1cccc(C(F)(F)F)c1] | 1-(4-Bromophenyl)-3-(Methyl([3-(Trifluoromethyl)Benzoyl]Oxy)Amino)-2-Prop+ En-1-One | |
| 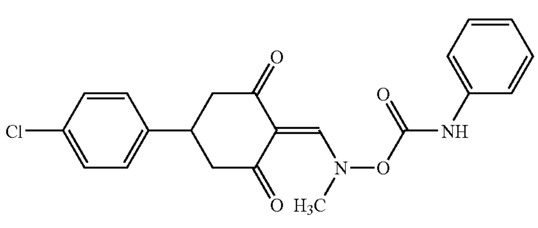 [SMILES: CN(C=C1C(=O)CC(c2ccc(Cl)cc2)CC1=O)OC(=O)Nc1ccccc1] | 2-([[(Anilinocarbonyl)Oxy](Methyl)Amino]Methylene)-5-(4-Chlorophenyl)-1,3+-Cyclohexanedione | |

TABLE 1-continued

Commercially-available —N—O•, —N—OH or N=O containing groups

| Structure | Name | CAS No. |
|---|---|---|
| 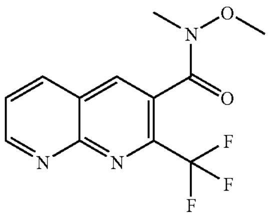 [SMILES: CON(C)C(=O)c1cc2cccnc2nc1C(F)(F)F] | N-Methoxy-N-Methyl-2-(Trifluoromethyl)-1,8-Naphthyridine-3-Carboxamide | |
| 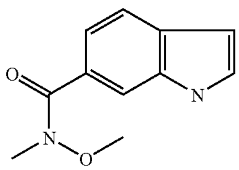 | N-Methoxy-N-Methyl-Indole-6-Carboxamide | |
| 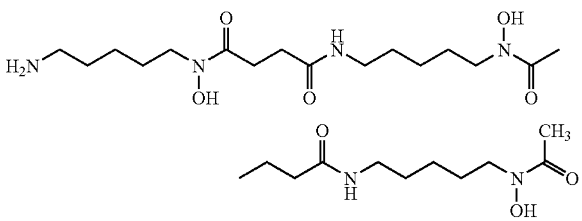 | Desferrioxamin | |
| 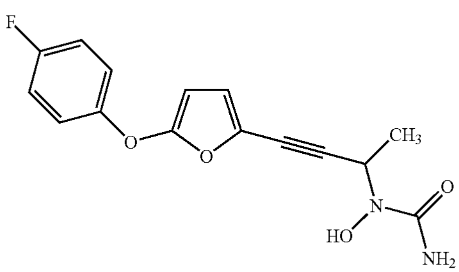 [SMILES: CC(C#Cc1ccc(Oc2ccc(F)cc2)o1)N(O)C(N)=O] | AKOS 91254 | 127408-31-5 |
| 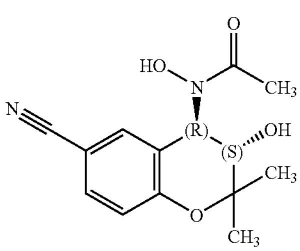 | N-[(3s,4r)-6-Cyano-3,4-Dihydro-3-Hydroxy-2,2-Dimethyl-2h-1-Benzopyran-4-Y+L]-N-Hydroxyacetamide | 127408-31-5 |
| 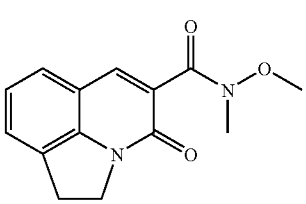 [SMILES: CON(C)C(=O)c1cc2cccc3c2n(c1=O)CC3] | N-Methoxy-N-Methyl-1,2-Dihydro-4-Oxo-Pyrrolo[3,2,1-Ij]Quinoline-5-Carboxa+Mide | |
| 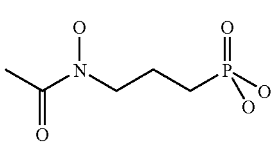 | Fr-900098 | |

TABLE 1-continued

Commercially-available —N—O•, —N—OH or N=O containing groups

| Structure | Name | CAS No. |
|---|---|---|
| 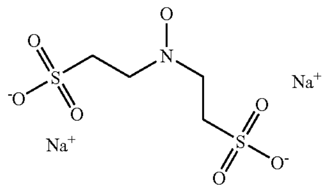 | 2,2'-(Hydroxyimino)Bis-Ethanesulfonic Acid Disodium Salt | 133986-51-3 |
| 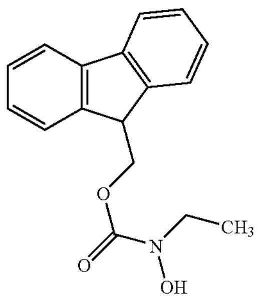 [SMILES: CCN(O)C(=O)OCC1c2ccccc2-c2ccccc21] | Fmoc-N-Ethyl-Hydroxylamine |  |
| 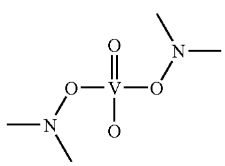 | Bis(N,N-Dimethylhydroxamido) Hydroxooxovanadate |  |
| 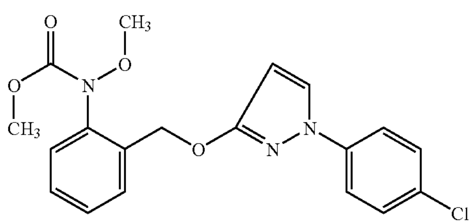 [SMILES: COC(=O)N(OC)c1ccccc1COc1ccn(-c2ccc(Cl)cc2)n1] | Pyraclostrobin | 175013-18-0 |
| 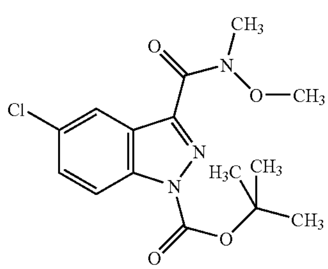 [SMILES: CON(C)C(=O)c1nn(C(=O)OC(C)(C)C)c2ccc(Cl)cc12] | 1-Boc-5-Chloro-3-(Methoxy-Methyl-Carbamoyl)Indazole |  |
| 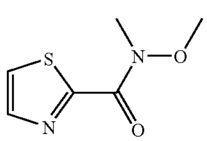 | N-Methoxy-N-Methyl-Thiazole-2-Carboxamide |  |
| 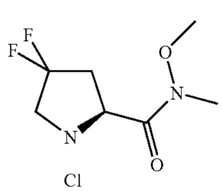 | 4,4-Difluoro-N-Methyl-N-Methoxy-L-Prolinamide Hcl |  |

TABLE 1-continued

Commercially-available —N—O•, —N—OH or N=O containing groups

| Structure | Name | CAS No. |
|---|---|---|
| 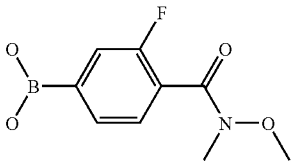 [SMILES: CON(C)C(=O)c1ccc(B(O)O)cc1F] | 3-Fluoro-4-(Methoxy(Methyl)Carbamoyl) Phenylboronic Acid | 913835-59-3 |
| 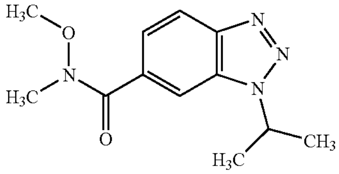 [SMILES: CON(C)C(=O)c1ccc2nnn(C(C)C)c2c1] | 1-Isopropyl-N-Methoxy-N-Methyl-1h-Benzo[D][1,2,3]Triazole-6-Carboxamide | 467235-06-9 |
| 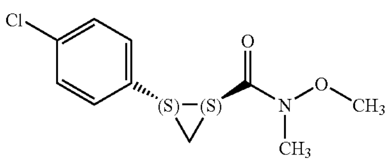 | (Trans)-2-(4-Chlorophenyl)-N-Methoxy-N-Methylcyclopropanecarboxamide | |
| 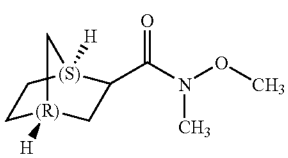 | Bicyclo[2.2.1]Heptane-2-Carboxylic Acid Methoxy-Methyl-Amide | |
| 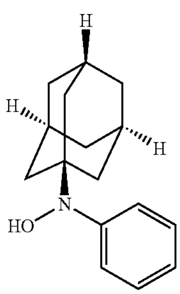 [SMILES: ON(c1ccccc1)[C@]12C[C@H]3C[C@H](C[C@H](C3)C1)C2] | Akos Bc-0582 | |
| 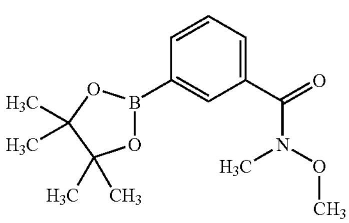 | 3-(N,O-Dimethylhydroxylaminocarbonyl) Phenylboronic Acid, Pinacol Ester | |
| 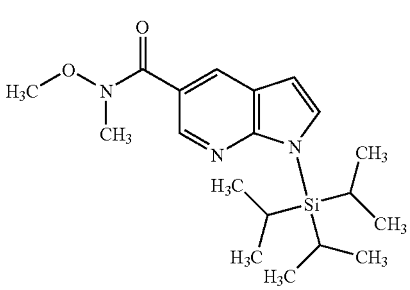 [SMILES: CON(C)C(=O)c1cnc2c(ccn2[Si](C(C)C)(C(C)C)C(C)C)c1] | 1-Triisopropylsilanyl-1h-Pyrrolo[2,3-B]Pyridine-5-Carboxylic Acid Methoxy+-Methyl-Amide | |

TABLE 2

| Examples of —N—O• (nitroxide) containing groups | | |
|---|---|---|
| Structure | Name | CAS No. |
| | G1 (Log P = 2.0) | |
| | G2 (Log P = 2.5) | |
| | G3, (Log P = 3.4) | |
| | G4 (Log P = 5.4) | |
| | G5 (Log P = 8.2) | |
| | G6 (Log P = 3.2) | |
| | TIPNO-1 (Tert-butyl isopropyl phenyl nitroxide-1; Log P = 3.9) | |

TABLE 2-continued

| Examples of —N—O• (nitroxide) containing groups | | |
|---|---|---|
| Structure | Name | CAS No. |
| | TIPNO-2 (Log P = 3.6) | |
| | TIPNO-3 (Log P = 4.8) | |
| | Bis-TIPNO (Log P = 7.3) | |
| | Nitronyl Nitroxide; 4-Phenyl-2,2,5,5-tetramethyl-3-imidazolin-1-yloxy (Log P = 1.7) | 39753-69-0 |
| | Doxyl radical (Log P = 2.6) | |
| | 3-carboxy PROXYL; 3-(Carboxy)-2,2,5,5-tetramethyl-1-pyrrolidinyloxy (Log P = 1.4) | 2154-68-9 |

TABLE 2-continued

Examples of —N—O• (nitroxide) containing groups

| Structure | Name | CAS No. |
|---|---|---|
| 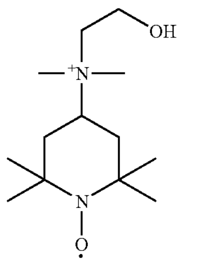 | TEMPO choline; 4-(N,N-Dimethyl-N-(2-hydroxyethyl))ammonium-2,2,6,6-tetramethylpiperidine-1-oxyl chloride (Log P = 2.5) | 50669-92-6 |
| 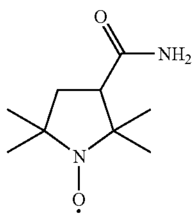 | 3-carbamoyl-PROXYL; 3-(Carbomoyl)-2,2,5,5-tetramethyl-1-pyrrolidinyloxy (Log P = 0.9) | 4399-80-8 |
| 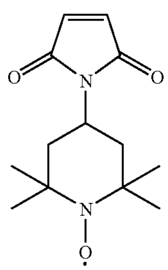 | 4-maleimido-TEMPO; 4-Maleimido-2,2,6,6-tetramethyl-1-piperidinyloxy (Log P = 2.9) | 15178-63-9 |
| 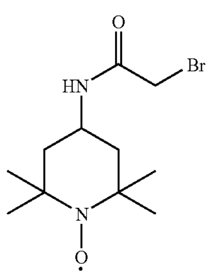 | 4-(2-bromoacetamido)-TEMPO; 4-(2-Bromoacetamido)-2,2,6,6-tetramethyl-1-piperidinyloxy (Log P = 1.9) | 24567-97-3 |

In another embodiment, the free radical-scavenging group comprises a mimetic of an enzyme or protein that scavenges ROS and/or RNS in vivo. Non-limiting examples of mimetics include manganese-based metalloporphyrin complexes, manganese-based salen complexes, ubiquinone analogs, ubiquinone analog fragment moieties, ubiquinone analog fragment moieties lacking a hydrophobic tail, superoxide dismutase mimetics, and catalase biomimetics. In yet another embodiment, the chemical moiety can be categorized by the property of inhibiting nitric oxide synthase enzyme activity. Non-limiting examples of NOS inhibitors include urea/guanidine derivatives, such as 2-amino-6-methyl-thiazine.

Nitroxide radicals exert SOD mimetic activity (Krishna M C, Russo A, Mitchell J B et al. Do nitroxide antioxidants act as scavengers of $O_2^-$ or as SOD mimics? J Biol Chem 1996, 271:26026-26031; Samuni A, Mitchell J B, DeGraff W et al. Nitroxide SOD-mimics: modes of action. Free Radic Res Commun 1991, 12-13 Pt 1:187-194), which contributes to the prevention of the reaction of $O_2^-$. with .NO, thereby inhibiting formation of the highly toxic species, peroxynitrite ($ONOO^-$). Nitroxide radicals, upon reacting with an electron, are reduced to the corresponding hydroxylamines, thereby generating a potent anti-oxidant. Thus, nitroxides combine several important antioxidant and electron-scavenging properties in a single functional moiety. In another non-limiting example, the free radical-scavenging group comprises a chemical group with both electron scavenging and antioxidant properties.

In the mitochondria-targeted electron scavenger, the free radical-scavenging group is linked covalently (attached) to a mitochondria-targeting group. Non-limiting examples of covalent linkages include an amide group, an ester group, or a carbon-carbon bond. The mitochondria-targeting group may be any moiety having such activity. In one non-limiting embodiment, the mitochondria-targeting group is a Gramicidin S polypeptide.

Gramicidin S is a membrane-active antibiotic and it is a cyclic decapeptide (see FIG. 1A), where the pentapeptide sequence Leu-$^D$Phe-Pro-Val-Orn is repeated twice (Kondejewski L H, Farmer S W, Wishart D S et al. Gramicidin S is active against both gram-positive and gram-negative bacteria. Int J Pept Protein Res 1996, 47:460-466). Antibiotics of this group have a high affinity for bacterial membranes (Scholtz K F, Solovjena N A, Kotelnikova A V et al. Effect of gramicidin S and its derivatives on the mitochondrial membrane. Febs Lett 1975, 58:141-144), and bacteria and mitochondria share numerous similarities (Berry S. Endosymbiosis and the design of eukaryotic electron transport. Biochim Biophys Acta 2003, 1606:57-72).

As used herein, the term "hemigramicidin" refers to a repeated peptide sequence within Gramicidin S. In one non-limiting embodiment, hemigramicidin refers to the pentapeptide sequence Leu-$^D$Phe-Pro-Val-Orn (e.g.:

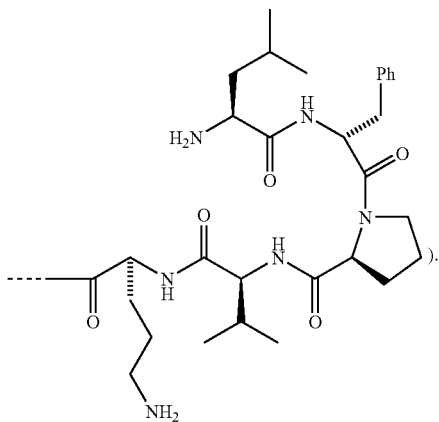

Figure 1A:
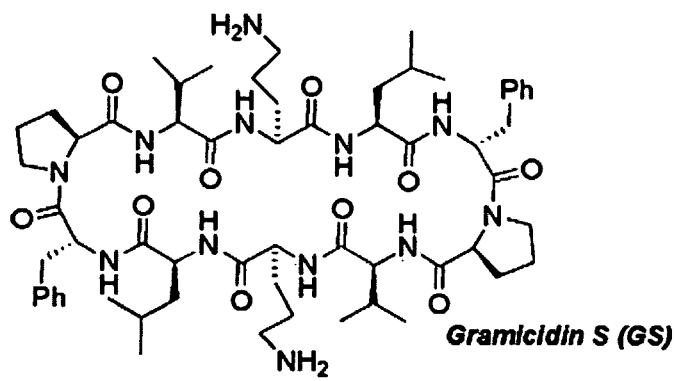
FIG. 1 shows schematically the chemical structures of gramicidin S (FIG. 1A), XJB-5-208 (FIG. 1B), and XJB-5-131 (FIG. 1C).

As Gramicidin S is cyclic, hemigramicidin may also refer to any sequential pentapeptide sequence within Gramicidin S, such as $^D$Phe-Pro-Val-Orn-Leu, Pro-Val-Orn-Leu-$^D$Phe, Val-Orn-Leu-$^D$Phe-Pro, and Orn-Leu-$^D$Phe-Pro-Val (see, e.g. FIG. 1A). Non-limiting examples of hemigramicidins are provided in US Patent Publication Nos. US-2007-0161573-A1 and US-2007-0161544-A1, and U.S. patent application Ser. No. 11/565,779, incorporated herein by reference in their entireties, but only to the extent that they provide and describe useful mitochondrial-targeted electron scavengers and mitochondria-targeting groups.

In reference to the peptide mitochondria-targeting group, the peptide may be modified to produce an analog of the peptide mitochondria-targeting group, for example, a hemigramicidin analog. Modified polypeptides are, in many instances, more stable than un-modified polypeptides because the modified residue(s) render the polypeptide resistant to protease cleavage/degradation. As such, by modification of the polypeptide backbone, including, without limitation, derivatization of one or more amino acids or attachment of chemical groups onto a polypeptide chain, the usefulness of a polypeptide-containing compound as a drug may be increased—the modification increasing drug parameters, such as bioavailability and half-life. A large number of potential modifications are listed, for example and without limitation, in U.S. Pat. No. 6,075,121, including use of α and β ester linkages, thioamines and N-hydroxylation.

A well-characterized polypeptide modification that shows substantial promise in producing polypeptides that retain function of the "parent" polypeptide, yet show better protease resistance is the use of "peptoids." A peptoid is a polypeptide containing one or more N-substituted glycine residues. An N-substituted amino acid residue has a standard amino acid side-chain pendant from the N, rather than from the a carbon. For example NVal has a 2-propyl group pendant from its N. N-alkyl glycine residues are common peptoid building blocks, which may mimic standard amino acids, such as Val (2-propyl), Leu (isobutyl) or Ile (2-butyl) among the 19 other standard R-group-containing amino acids, or which may contain virtually any R-group, for example any lower alkyl ($C_{1-6}$) group, alcohol, amine, organic acid (carboxyl-containing), etc. group. By including N-modified glycine residues, the peptoid is made resistant to proteolysis and may be functionalized in a manner that increases the peptide's bioavailability or tissue localization. U.S. Pat. No. 6,075,121 describes peptoid structures and methods of producing peptoids.

Conservative derivatives of a given peptide sequence are peptides in which native amino acids are replaced with amino acids that either have similar chemical properties, such as, without limitation, hydrophobicity, size, isoelectric point, molecular weight and H-bonding potential. Conservative derivatives substantially retain the function of the parent or reference sequence, which, in the context of this disclosure, means mitochondria-targeting ability. Of course, the derivative may have superior mitochondria-targeting activity as compared to the reference or parent sequence. Conservative derivatives may be determined empirically by testing in an intended use for the peptide and finding no substantial loss of function in its use (such as in the case of a mitochondria-targeting group in its ability to target mitochondria, as disclosed herein and/or in reference to substitution frequency in homologous proteins).

Amino acid substitutions in conservative derivatives include any art-recognized conservative substitutions, typically expressed in the form of a scoring matrix. For example and without limitation, the substitution is determined in reference to a Blosum62 Substitution matrix. Other art-recognized scoring matrices include, without limitation other BLOSUM (Blocks Substitution Matrix) matrices, such as, without limitation BLOSUM 45, 52, 60, 80 or 90 (the higher the number, the less divergent the "matches"), PAM (Point Accepted Mutation) matrices, such as, without limitation, PAM 100, 120, 160, 200 and 250 (the higher the number, the more divergent the "matches"), GONNET matrices and DNA identity matrices. Using the BLOSUM62 matrix, the following amino acids are considered conservative substitutions: Met, Ile, Val, Phe and Ala for Leu; Ile, Met, Leu, Ala and Thr for Val and Tyr, Trp, Leu, Ile and $^D$Met for $^D$Phe. Substitutions for Orn might include Met, Lys and Arg. In yet another embodiment, one or more of the Leu, Val or Orn residues are substituted with any amino acid. Lastly, any 1, 2 or 3 or more amino acids may be substituted conservatively or non-conservatively with another amino acid, so long as mitochondria-targeting function is retained.

The mitochondria-targeting group described herein can be derived from hemigramicidin ("hemigramicidin derivative"). The hemigramicidin derivative mitochondria-targeting group can comprise two or more sequential amino acids from hemigramicidin. The targeting group can also comprise modifications to the hemigramicidin-derived sequence. Non-limiting examples of these modifications include chemical or biochemical modifications to one or more amino acids, to one or more bonds between the amino acids, to bonds between the targeting group and the free radical-scavenging group. In one non-limiting embodiment, one or more amino acids are N-acylated. Non-limiting examples of acylating agents include: aryloxycarbonyl agents, such as benzyloxycarbonyl (Cbz) and fluorene-9-methyloxycarbonyl (FMOC) agents; and alkyloxycarbonyl agents, such as tert-butoxycarbonyl (Boc), methoxycarbonyl, and trichloroethoxycarbonyl agents. In one non-limiting example, the Leu of hemigramicidin is N-acylated with a Boc acyl group and the Orn is N-acylated with a Cbz acyl group. In another non-limiting example, the mitochondria-targeting group comprises a hemigramicidin derivative:

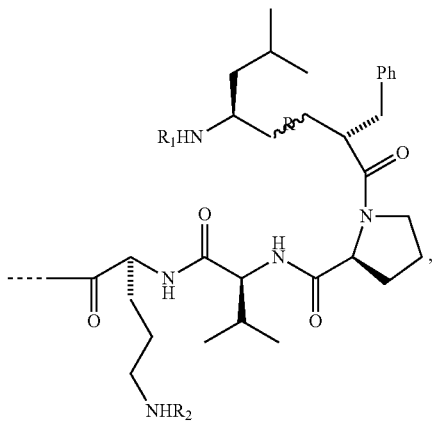

where R represents the bond between the Leu and $^D$Phe amino acids, and $R_1$ and $R_2$ represent H, or chemical modifications to the targeting group, such as by an acyl group. In yet another non-limiting example, the mitochondria-targeting group comprises a hemigramicidin derivative:

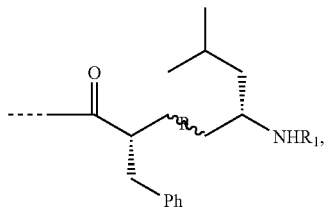

where R represents the bond between the Leu and $^D$Phe amino acids, and $R_1$ represents H, or chemical modifications to the targeting group, such as by an acyl group.

An amino acid or other compound is said to be "N-acylated" with one or more of an acylating agent when an amine group of the amino acid or compound is reacted with another compound to form a carbamide bond of —N—C(=O)—. In one non-limiting example, when the acylation agent is a benzyloxycarbonyl agent, the acyl group is —C(=O)O-benzyl. In a further non-limiting example, when the acylating agent is a benzyloxycarbonyl agent and the amino acid to be N-acylated is Orn, then the N-acylated amino acid is designated as Orn(Cbz). In yet another non-limiting example, when the acylation agent is a tert-butoxycarbonyl agent, the acyl group is —C(=O)O-tert-butyl.

In another non-limiting embodiment of a hemigramicidin derivative, one or more of the peptide bonds between the amino acids are replaced to form a peptide isostere. Among suitable peptide isosteres are tri-substituted (E)-alkene peptide isosteres and cyclopropane peptide isosteres, as well as all imine addition products of hydrometalated and carbometalated internal and terminal alkynes for the synthesis of di- and tri-substituted (E)-alkene and cyclopropane peptide isosteres (see, for example, Wipf et al. Imine additions of internal alkynes for the synthesis of trisubstituted (E)-alkene and cyclopropane peptide isosteres. Adv Synth Catal. 2005, 347(11-13):1605-13). These peptide mimetics have been found to act as β-turn promoters (Wipf et al. Convergent approach to (E)-alkene and cyclopropane peptide isosteres. Org. Lett. 2005, 7(1):103-6).

A Leu-$^D$Phe-Pro-Val-Orn hemigramicidin fragment encompasses a β-turn motif that directs most of the polar functionality of the peptide strand into the core. For example and without limitation, a graphic representation of the Leu-$^D$Phe-Pro-Val-Orn hemigramicidin fragment encompassing a β-turn motif is given below:

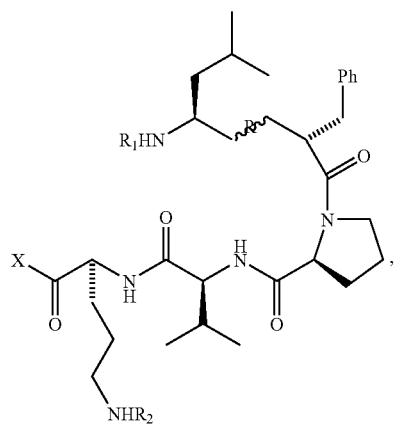

where X represents the free-radical scavenging group and the covalent linkage between the free-radical scavenging group and the mitochondria-targeting group, R represents the bond between the Leu and $^D$Phe amino acids, and $R_1$ and $R_2$ represent H, or chemical modifications to the targeting group, such as by an acyl group.

In one non-limiting embodiment, the targeting group used comprises Leu-$^D$Phe-Pro-Val-Orn. In one non-limiting embodiment, the targeting group used comprises Leu-$^D$Phe-Pro-Val-Orn with an amide bond between the Leu and $^D$Phe amino acids. For example and without limitation, the mitochondria-targeted electron scavenger comprises:

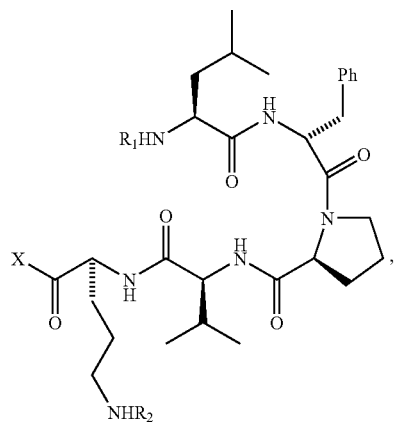

where X represents the free-radical scavenging group and the covalent linkage between the free-radical scavenging group and the mitochondria-targeting group, R is an amide bond, and $R_1$ and $R_2$ represent H, or chemical modifications to the targeting group, such as by an acyl group.

In another non-limiting embodiment, the targeting group comprises an (E)-alkene bond to form Leu-[(E)-CH=CH]-$^D$Phe-Pro-Val-Orn. For example and without limitation, the mitochondria-targeted electron scavenger comprises:

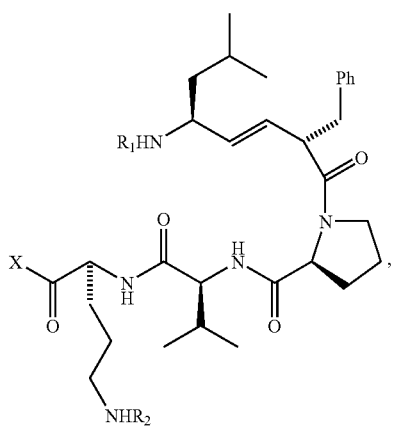

where X represents the free-radical scavenging group and the covalent linkage between the free-radical scavenging group and the mitochondria-targeting group, R is an (E)-alkene bond of (E)-CH=CH, and $R_1$ and $R_2$ represent H, or chemical modifications to the targeting group, such as by an acyl group. For example and without limitation, the mitochondria-targeted electron scavenger comprises:

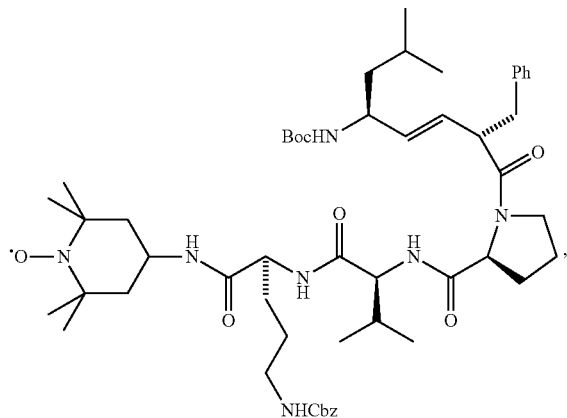

where X is the free-radical scavenging group of TEMPO and the covalent linkage between TEMPO and the mitochondria-targeting group is an amide group, R is an (E)-alkene bond of (E)-CH=CH, $R_1$ is a tert-butoxycarbonyl (Boc) acyl group, and $R_2$ is a benzyloxycarbonyl (Cbz) acyl group.

In another non-limiting embodiment, the targeting group comprises an (E)-alkene bond to form Leu-[(E)-CH=C(CH$_3$)]-$^D$Phe-Pro-Val-Orn. For example and without limitation, the mitochondria-targeted electron scavenger comprises:

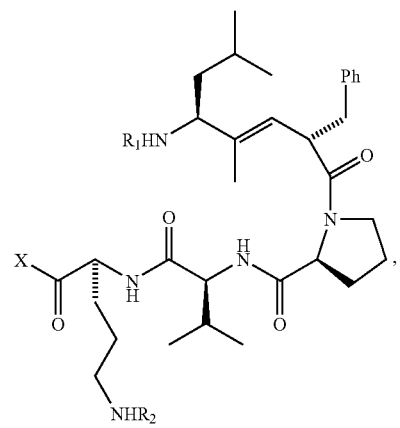

where X represents the free-radical scavenging group and the covalent linkage between the free-radical scavenging group and the mitochondria-targeting group, R is an (E)-alkene bond of (E)-CH=C(CH$_3$), and $R_1$ and $R_2$ represent H, or chemical modifications to the targeting group, such as by an acyl group.

In yet another non-limiting embodiment, the targeting group comprises a cyclopropane

ring to form Leu-[Cp]-$^D$Phe-Pro-Val-Orn. For example and without limitation, the mitochondria-targeted electron scavenger comprises:

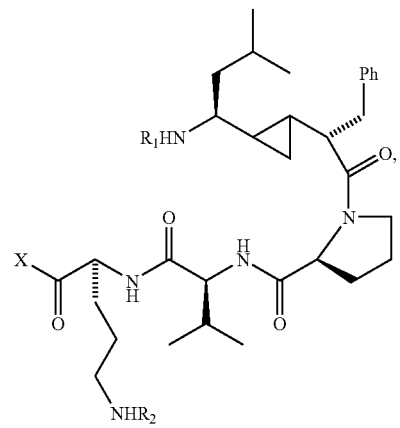

where X represents the free-radical scavenging group and the covalent linkage between the free-radical scavenging group and the mitochondria-targeting group, R is a cyclopropane ring, and $R_1$ and $R_2$ represent H, or chemical modifications to the targeting group, such as by an acyl group.

The targeting group can also be as short as two amino acids and yet maintain selectivity for the mitochondria. For example and without limitation, the targeting group comprises Leu-$^D$Phe and mitochondria-targeted electron scavenger comprises:

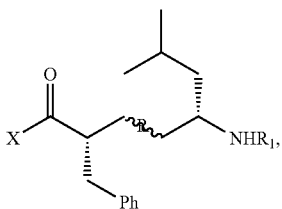

where X represents the free-radical scavenging group and the covalent linkage between the free-radical scavenging group and the mitochondria-targeting group, R represents the bond between the Leu and $^D$Phe amino acids, and $R_1$ represents H or chemical modifications to the targeting group, such as by an acyl group. In one non-limiting embodiment, the targeting group comprises an amide bond to form

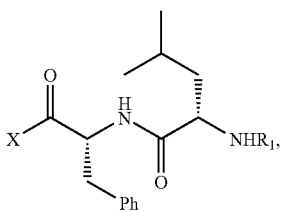

where X represents the free-radical scavenging group and the covalent linkage between the free-radical scavenging group and the mitochondria-targeting group, R is an amide bond (or peptide bond), and $R_1$ represents H or chemical modifications to the targeting group, such as by an acyl group.

In another non-limiting embodiment, the targeting group comprises an (E)-alkene bond to form Leu-[(E)-CH=CH]-$^D$Phe. For example and without limitation, the mitochondria-targeted electron scavenger comprises:

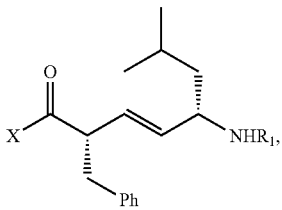

where X represents the free-radical scavenging group and the covalent linkage between the free-radical scavenging group and the mitochondria-targeting group, R is an (E)-alkene bond of (E)-CH=CH, and $R_1$ represents H or chemical modifications to the targeting group, such as an acyl group. For example and without limitation, the mitochondria-targeted electron scavenger comprises:

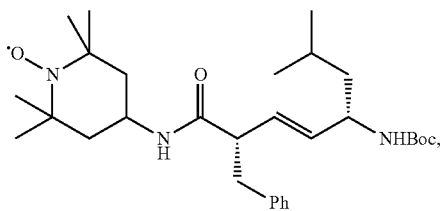

where X is the free-radical scavenging group of TEMPO and the covalent linkage between TEMPO and the mitochondria-targeting group is an amide group, R is an (E)-alkene bond of (E)-CH=CH, and $R_1$ is the tert-butoxycarbonyl (Boc) acyl group. In yet another non-limiting embodiment, the targeting group comprises a cyclopropane ring to form Leu-[Cp]-$^D$Phe. For example and without limitation, the mitochondria-targeted electron scavenger comprises:

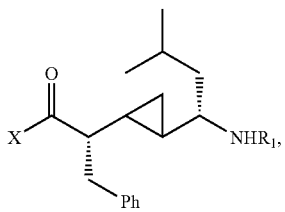

where X represents the free-radical scavenging group and the covalent linkage between the free-radical scavenging group and the mitochondria-targeting group, R is a cyclopropane ring, and $R_1$ represents H or chemical modifications to the targeting group, such as by an acyl group.

In one non-limiting embodiment, the membrane active peptidyl fragment is derived from an antibiotic. The fragment may be from an antibiotic molecule that acts by targeting a bacterial cell wall. The antibiotic may be chosen from one or more of: a bacitracin, a gramicidin, a valinomycin, an enniatin, an alamethicin, a beauvericin, a serratomolide, a sporidesmolide, a tyrocidin, a polymyxin, a monamycin, and a lissoclinum peptide, or an analog or conservative derivative thereof that is able to target mitochondria.

The mitochondria-targeted electron scavenger can be prepared in any useful manner. For example and without limitation, the targeting group can be prepared by a peptide synthesis technique. In another non-limiting example, the targeting group can be prepared by an organometallic synthesis technique.

Isosteres are molecules or fragments that exhibit related conformational, steric, and or electronic properties. As a result, they can also exhibit similar pharmacokinetic and pharmacodynamic properties. Non-limiting examples of isosteres are fluorine↔hydrogen and carbon dioxide ↔ nitrous oxide modifications.

In one non-limiting example, a dipeptide isostere of the mitochondria-targeted electron scavenger is prepared by the following synthetic steps (see, Wipf et al. Mitochondrial targeting of selective electron scavengers: synthesis and biological analysis of hemigramicidin-TEMPO conjugates. *J Am Chem Soc* 2005, 127:12460-12461). First, a functionalized alkyne is coupled to a functionalized imine by a hydrozirconation and bimetallic Zr/Zn transmetalation step to form allylic amides. Second, the allylic amide products are separated to obtain only one chiral product. Third, the terminal alcohol group of the separated product is oxidized to a carboxylic acid, thus completing a dipeptide isostere containing an (E)-alkene bond. Fourth, the dipeptide isostere is coupled to a free radical-scavenging group to form the mitochondria-targeted electron scavenger. As necessary, these steps can include additional methods to aid in synthesis, such as, for example and without limitation, separation steps, protection of reactive groups, purification steps, and work up steps. In one non-limiting example, the functionalized imine is N-Boc-isovaleraldimine, the dipeptide isostere of the mitochondria-targeted electron scavenger is N-Boc-Leu-[(E)-

Figure 1B:
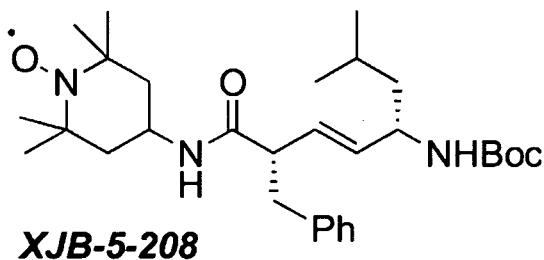

CH=CH]-$^D$Phe and the mitochondria-targeted electron scavenger comprises N-Boc-Leu-[(E)-CH=CH]-$^D$Phe-N-TEMPO (XJB-5-208, as shown in FIG. 1B).

Figure 1C:
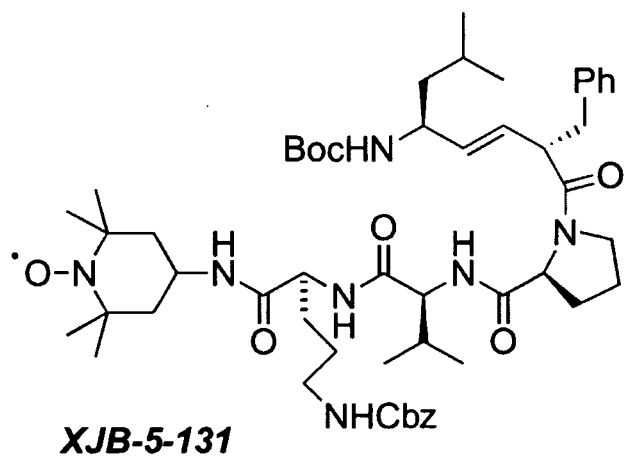

In another non-limiting embodiment, a peptide isostere of the mitochondria-targeted electron scavenger is prepared by the following synthetic steps. First, a functionalized alkyne is coupled to a functionalized imine by a hydrozirconation and bimetallic Zr/Zn transmetalation step to form allylic amides. Second, the allylic amide products are separated to obtain only one chiral product. Third, the terminal alcohol group of the separated product is oxidized to a carboxylic acid, thus completing a dipeptide isostere containing an (E)-alkene bond. Fourth, a tripeptide is linked to the dipeptide isostere using 1-ethyl-3-(3-dimethylaminopropyl carbodimide hydrochloride) as a coupling agent to form a pentapeptide product. Fifth, the pentapeptide product is saponified and coupled to a free radical-scavenging group to form the mitochondria-targeted electron scavenger. As necessary, these steps can include additional methods to aid in synthesis, such as, for example and without limitation, separation steps, protection of reactive groups, purification steps, and work up steps. For example and without limitation, the pentapeptide product is N-Boc-Leu-[(E)-CH=CH]-$^D$Phe-Pro-Val-Orn(Cbz)-OMe and the mitochondria-targeted electron scavenger comprises N-Boc-Leu-[(E)-CH=CH]-$^D$Phe-Pro-Val-Orn(Cbz)-N-TEMPO (XJB-5-131, as shown in FIG. 1C).

The recited method above can be used to form a mitochondria-targeted electron scavenger with more than five peptide sequences. For example and without limitation, the fourth step can recite linking a tetrapeptide to the dipeptide isostere and forming a hexapeptide. In another non-limiting example, the fourth step recites linking a hexapeptide to the dipeptide isostere and forming an octapeptide.

Rather than an (E)-alkene bond, the mitochondria-targeted electron scavenger can comprise a cyclopropane ring. In one non-limiting embodiment, a dipeptide isostere of the mitochondria-targeted electron scavenger is prepared by the following synthetic steps (see, Wipf et al. Adv. Synth. Catal. 2005, 347: 1605-13). First, a functionalized alkyne is coupled to a functionalized imine and $CH_2I_2$ by a hydrozirconation and bimetallic Zr/Zn transmetalation step to form aminocyclopropanes. Second, the aminocyclopropane products are separated to obtain only one chiral product. Third, the terminal alcohol group of the separated product is oxidized to a carboxylic acid, thus completing a dipeptide isostere containing a cyclopropane ring. Fourth, the dipeptide isostere is coupled to a free radical-scavenging group to form the mitochondria-targeted electron scavenger. As necessary, these steps can include additional methods to aid in synthesis, such as, for example and without limitation, separation steps, protection of reactive groups, purification steps, and work up steps. For example and without limitation, the dipeptide isostere of the mitochondria-targeted electron scavenger is N-Boc-Leu-[Cp]-$^D$Phe and the mitochondria-targeted electron scavenger comprises N-Boc-Leu-[Cp]-$^D$Phe-N-TEMPO.

In another non-limiting embodiment, a peptide isostere of the mitochondria-targeted electron scavenger is prepared by the following synthetic steps (see, Wipf et al. Adv. Synth. Catal. 2005, 347: 1605-13). First, a functionalized alkyne is coupled to a functionalized imine and $CH_2I_2$ by a hydrozirconation and bimetallic Zr/Zn transmetalation step to form aminocyclopropanes. Second, the aminocyclopropane products are separated to obtain only one chiral product. Third, the terminal alcohol group of the separated product is oxidized to a carboxylic acid, thus completing a dipeptide isostere containing a cyclopropane ring. Fourth, the dipeptide isostere is coupled to a free radical-scavenging group to form the mitochondria-targeted electron scavenger. Fifth, the pentapeptide product is saponified and coupled to a free radical-scavenging group to form the mitochondria-targeted electron scavenger. As necessary, these steps can include additional methods to aid in synthesis, such as, for example and without limitation, separation steps, protection of reactive groups, purification steps, and work up steps. For example and without limitation, the pentapeptide product is N-Boc-Leu-[Cp]-$^D$Phe-Pro-Val-Orn(Cbz)-OMe and the mitochondria-targeted electron scavenger comprises N-Boc-Leu-[Cp]-$^D$Phe-Pro-Val-Orn(Cbz)-N-TEMPO.

The recited method above can be used to form a mitochondria-targeted electron scavenger with a peptide sequence longer than a pentapeptide. For example and without limitation, the fourth step can recite linking a tetrapeptide to the dipeptide isostere and forming a hexapeptide. In another non-limiting example, the fourth step recites linking a hexapeptide to the dipeptide isostere and forming an octapeptide.

The mitochondria-targeted electron scavenger can be distributed to patients, health-care providers and otherwise commercially distributed as a drug product. The composition of the drug product comprises a mitochondria-targeted electron scavenger in a pharmaceutically-acceptable carrier. The mitochondria-targeted electron scavenger is present in the drug product in an amount effective to treat inflammation in a patient. Non-limiting examples of a suitable drug product include: an intravenous drug product comprising the mitochondria-targeted electron scavenger, for example and without limitation, from about 1 µmoles to 10 mmoles of the mitochondria-targeted electron scavenger per mL in water, PBS (Phosphate-buffered saline), normal saline, TRIS buffer, etc., an oral dosage form comprising the mitochondria-targeted electron scavenger, for example and without limitation from about 1 µmoles to 10 mmoles of the mitochondria-targeted electron scavenger in a suitable solid or liquid carrier, in for example and without limitation, in liquid, topical, capsule or tablet form, for example as a solid (including time release, fast-dissolving, etc.), an ointment or a liquid in a water, oil, a micellular dosage form (multi-phase, typically comprising a lipophilic or amphiphilic component such as oil, phospholipids or other amphiphilic compounds and, optionally, an aqueous component for forming a micellular or liposome structure either in the drug product or upon contact with aqueous compositions upon release in a patient), a homogenate, etc. As can be appreciated by those in the formulary arts, the choice of dosage form and typical ingredients are typically a matter of design choice and optimization, depending on the route of administration, whether the mitochondria-targeted electron scavenger is a salt or free base, the desired pharmacokinetics, the pharmacodynamics of the mitochondria-targeted electron scavenger, etc. The mitochondria-targeted electron scavenger drug product may be packaged in a commercially and pharmaceutically acceptable container, such as an intravenous drug pouch for a liquid or solid (e.g., lyophilized, dried, glassified, etc.) intravenous drug product, or a suitable vial, blister pack, bottle etc. for an oral drug product. Thus provided is a kit comprising one or more unit doses for treating inflammation in a patient, the unit doses comprising a mitochondria-targeted electron scavenger in an amount effective to treat the inflammation in a pharmaceutically acceptable carrier in a container.

EXAMPLES

Provided herein are examples of using a mitchondria-targeted electron scavenger both in vitro and in vivo to ameliorate effects from inflammation. Inflammation was induced by exposure to or injection of lipopolysaccharide (LPS) both in the presence or absence of XJB-5-131 (FIG. 1C) or XJB-5-208 (FIG. 1B). For in vitro studies using cell cultures, nitrite concentrations as an indicator of .NO production and HMGB1 by Western blot were measured in cell supernatants. For in vivo studies using mice, nitrite concentrations within blood and iNOS expression in liver, heart, lung and kidney samples were measured.

Example 1

Effect of XJB-5-131 and XJB-5-208 on Nitric Oxide Secretion In Vitro

Materials.

All chemicals were from Sigma-Aldrich (St Louis, Mo.) unless otherwise noted. The hemigramicidin-based compounds were synthesized as previously described (Wipf P, Xiao J, Jiang J et al. J Am Chem Soc 2005, 127:12460-12461). Dulbecco's modified Eagle medium (DMEM) was from BioWhittaker (Walkersville, Md.). Fetal bovine serum (FBS; <0.05 endotoxin units/ml) was from Hyclone (Logan, Utah). Pyrogen-free sterile normal saline solution was from Baxter (Deerfield, Ill.). Phosphate-buffered saline solution (PBS) was from Cambrex Bio Science (Walkersville, Md.).

Cells.

RAW 264.7 cells were obtained from the American Type Culture Collection (Manassas, Va.). Cells were maintained in DMEM supplemented with 10% FBS, 100 units/ml penicillin, and 100 µg/ml streptomycin at 37° C. in a humidified incubator (5% $CO_2$, 95% air). For stimulation experiments, cells were transferred to 24-well polystyrene culture plates (Corning Life Sciences, Corning, N.Y.) at 0.3 or $1\times10^6$ cells/well (depending on the experiment) in 1 ml of medium per well. After overnight incubation, the medium was removed and replaced with DMEM containing 0.25% FBS. Cells were stimulated by adding 0.1 µg/ml to 1 µg/ml *Escherichia coli* 0111:B4 lipopolysaccharide (LPS) in the presence or absence of graded concentrations of XJB-5-131 or XJB-5-208.

Nitrite Assay.

Nitrite ($NO_2^-$) concentrations were measured in cell supernatants and blood serum as an indicator of nitric oxide (.NO) production, where .NO readily oxidize into nitrites ($NO_2^-$) and nitrates ($NO_3^-$). The total concentration of .NO was determined by reducing $NO_3^-$ to $NO_2^-$ using cadmium and detecting $NO_2^-$ using the Greiss reagent and potassium nitrite as a standard.

Samples (200 µL) were incubated with 30% zinc sulfate to precipitate proteins and then centrifuged (4° C., 12,000 g, 5 min). Supernatants were added to 0.6 g activated cadmium (previously washed twice with each deionized $H_2O$, 0.1 M HCl, and 0.1 $NH_4OH$) and allowed to shake overnight at room temperature. The supernatants were removed. Greiss reagent (100 µL) was mixed with an equal volume of supernatant. Reaction between the Greiss reagent and $NO_2^-$ yielded an azo dye that can be detected spectrophotometrically. Absorbance was measured at 550 nm using a Packard Fusion™ microplate reader (PerkinElmer, Wellesley, Mass.).

Statistics and Data Presentation.

Calculations were performed using SPSS (SPSS Inc., Chicago, Ill.) and Stata 8SE (Stata Corporation, College Station, Tex.) software. Results were transformed into normally distributed variables when appropriate. Comparisons of parameters across experimental groups were made using analysis of variance and Fisher's Least Significant Difference Test or Kruskal Wallis and Mann-Whitney tests. A p value of less than 0.05 was taken to indicate statistical significance. Data are presented as mean±SEM.

Figure 2A:
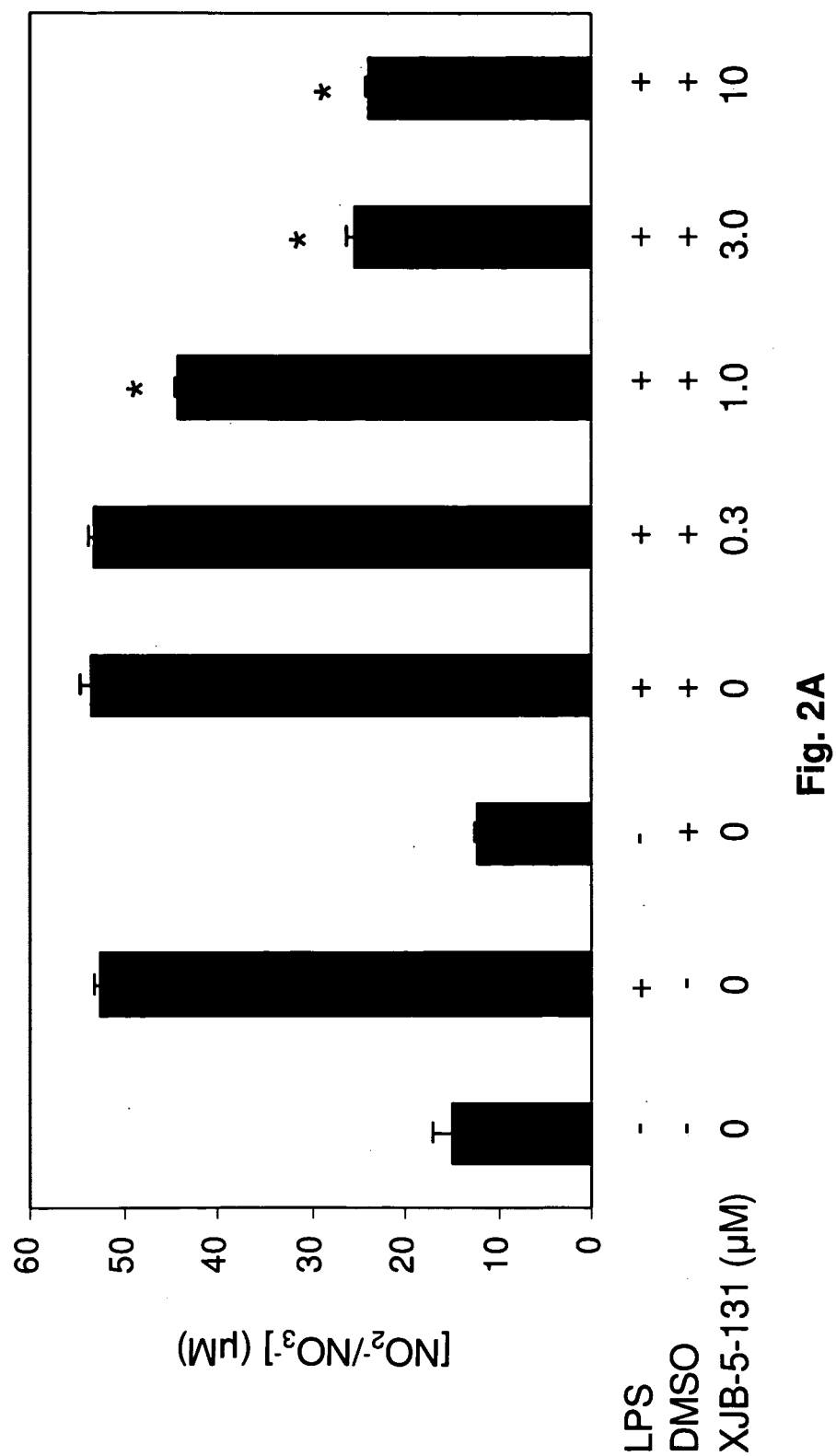
FIGS. 2A-2B are graphs showing nitric oxide secretion by lipopolysaccharide (LPS)-stimulated RAW 264.7 cells. Nitric oxide secretion was measured by detecting nitrite and nitrate ($NO_2^-/NO_3^-$) within cell lysates.
Figure 2B:
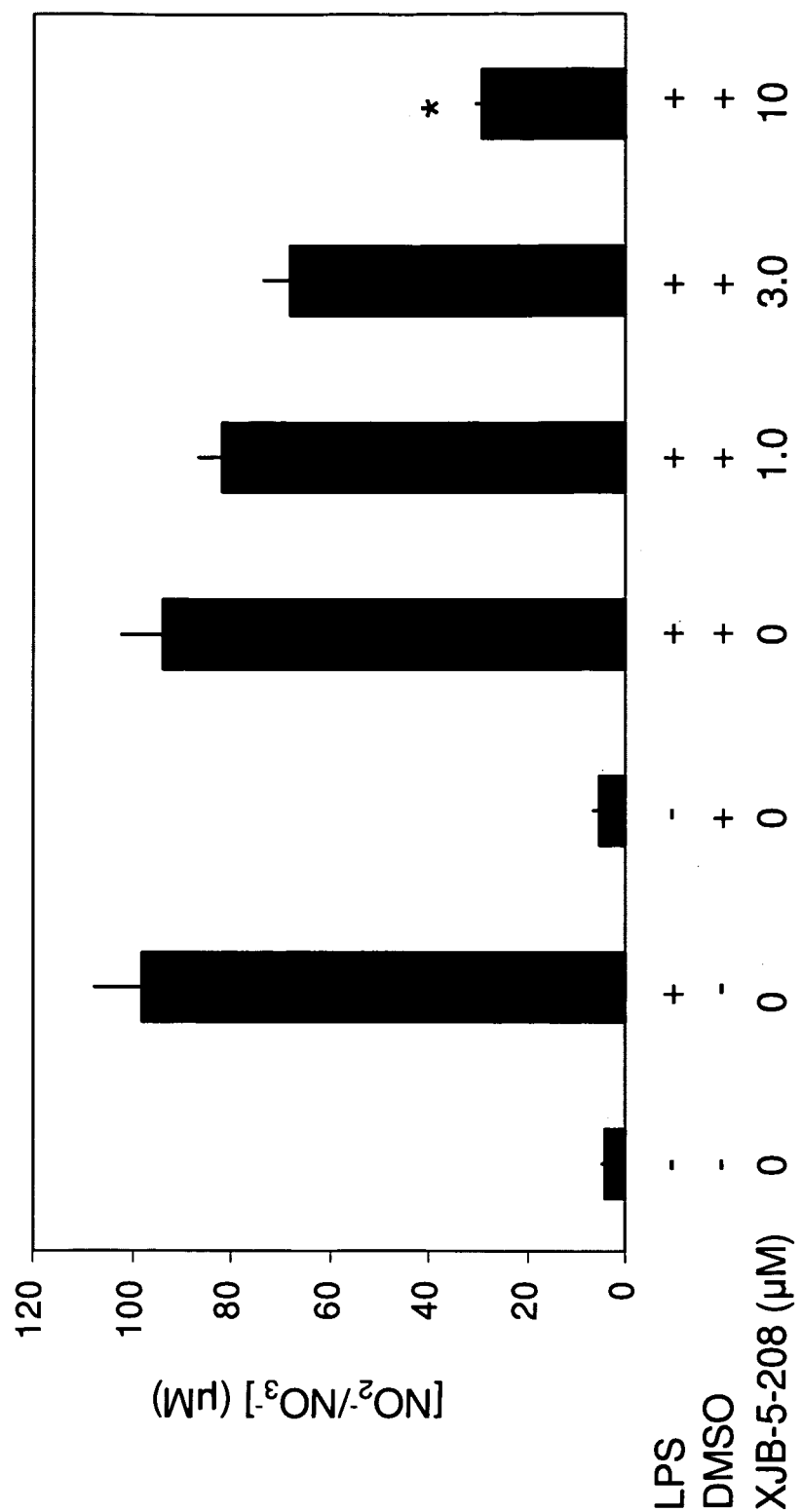

RAW 264.7 murine macrophage-like cells were incubated in the presence or absence of graded concentrations of XJB-5-131 or XJB-5-208. Concentrations of either XJB-5-131 or XJB-5-208 were dissolved in dimethyl sulfoxide (DMSO). During these experiments, the highest concentration of DMSO remaining in the cell culture was 0.18% (v/v). DMSO alone at this concentration had no effect on nitric oxide production by unstimulated cells or cells stimulated with LPS (FIGS. 2A and 2B, third and fourth bars from left). After one hour, LPS (100 or 1000 ng/ml) was added to the culture media. After 24 hours, culture supernatants were assayed for $NO_2^-$ plus $NO_3^-$ concentration, a marker of NO production. LPS induced a significant increase in .NO secretion by RAW 264.7 cells (FIGS. 2A and 2B).

NO secretion was significantly reduced by both XJB-5-131 (FIG. 2A) and XJB-5-208 (FIG. 2B) in a concentration-dependent manner. The approximate $IC_{50}$ for inhibition of LPS-induced NO production was 3 µM for XJB-5-131. The approximate $IC_{50}$ for inhibition of LPS-induced NO production was between 3 µM to 10 µM for XJB-5-131. Results depicted are representative of an experiment.

In use, the described mitochondria-targeting radical scavengers compounds can be formulated into a dosage form and distributed commercially. Provided therefore, is a kit comprising a mitochondria-targeting radical scavenger Example 2

Effect of XJB-5-131 and XJB-5-208 on Expression of iNOS In Vitro

Real-Time RT-PCR to Measure Steady-State iNOS Transcript Levels.

RAW 264.7 cells and liver tissue specimens were lysed with TRI-Reagent® (Molecular Research Center, Cincinnati, Ohio). Bromochloropropane (0.5 mL) was added in order to extract total RNA. After vigorous agitation and centrifugation (4° C., 12,000 g, 12 min), the aqueous phase containing RNA was collected. The RNA was precipitated with isopropanol (0.5 mL). The pellet was washed with 75% ethanol (1 mL) and centrifuged (4° C., 12,000 g, 5 min) twice, and then dissolved in RNA-free water. Total RNA was quantified using UV spectrophotometry (GeneQuant™ pro, GE Healthcare). Extracted RNAs (1 µg/reaction) were converted to single-strand cDNAs in a 20 µL volume reaction, using the Reverse Transcriptase System Kit (Promega, Madison, Wis.) as directed by the manufacturer. In a Gene Amp® PCR System 9700 (Applied Biosystems, Foster City, Calif.), the mixture was heated to 70° C. for 10 min, maintained at 42° C. for 30 min, and then heated to 95° C. for 5 min to terminate the reaction. TaqMan® Gene Expression Assays (Applied Biosystems) for 18S (endogenous control) and mouse iNOS were used. Reaction mixtures for PCR were assembled as follows: 10 µL TaqMan® Universal PCR Master Mix (Applied Biosystems), 1 µL of each assay, 5 µL cDNA template, and 3 µL of water. PCR reactions were performed in a thermocycler 7300 Real Time PCR System (Applied Biosystems) under recommended conditions (50° C. for 2 min; 95° C. for 10 min; 95° C. for 15 s; 60° C. for 1 min). The two last steps were repeated for 40 cycles. Each sample was assayed in duplicate and the values were averaged. The $\Delta C^T$ relative quantification method was used to calculate mRNA levels for iNOS in the samples, as previously described (Scharte M, Han X, Bertges D J et al. Cytokines induce HIF-1 DNA binding and the expression of HIF-1-dependent genes in cultured rat enterocytes. Am J Physiol Gastrointest Liver Physiol 2003, 284: G373-G384). Results were normalized relative to 18S rRNA expression levels.

RAW 264.7 cells were incubated in presence or absence of graded concentrations of XJB-5-131 or XJB-5-208. Concentrations of either XJB-5-131 or XJB-5-208 were dissolved in dimethyl sulfoxide (DMSO). During these experiments, the highest concentration of DMSO remaining in the cell culture was 0.05% (v/v). DMSO alone at this concentration had no effect on nitric oxide production by unstimulated cells or cells stimulated with LPS (FIGS. 3A and 3B, third and fourth bars from left). After one hour, LPS (100 ng/ml) was added to the culture media. After 24 hours, steady-state levels of iNOS mRNA were measured using real-time quantitative RT-PCR.

Incubating the cells with LPS induced a significant increase in iNOS mRNA expression (FIGS. 3A and 3B). However, co-incubation with either XJB-5-131 (FIG. 3A) or XJB-5-208 (FIG. 3B) inhibited LPS-induced iNOS up-regulation. XJB-5-131 was more potent in this regard than XJB-5-208. Results depicted are representative of an experiment, which was repeated three times with similar findings.

Example 3

Effect of XJB-5-131 on HMGB1 Secretion In Vitro

HMGB1 Western Blot.

Equal volumes of cell culture supernatants were mixed with Laemmli buffer (20% glycerol, 10% beta-mercaptoethanol, 5% SDS, 0.2 M Tris.HCl, pH 6.8, and 0.4% bromophenol blue). After boiling for 10 min, the samples were subjected to 10% SDS-polyacrylamide gel electrophoresis. The resolved proteins were transferred to Hybond™-P polyvinylidene difluoride membranes (GE Healthcare, Chalfont St. Giles, UK), and blocked with bovine lacto-transfer optimizer buffer (1×PBS, 5% nonfat milk, and 0.05% Tween® 20) for 1 h. The membranes were incubated overnight at 4° C. with a 1:2000 dilution of rabbit polyclonal anti-HMGB1 antibody (generously provided by Dr. Michael T. Lotze, University of Pittsburgh) in blocking buffer. After washing three times in 1×PBST (1×PBS with 0.3% Triton X-100), immunoblots were exposed at room temperature for 1 h to a 1:20,000 dilution of horseradish peroxidase-conjugated goat anti-rabbit secondary antibody (Sigma-Aldrich, St. Louis, Mo.). After washing three times with 1×PBST, the membranes were illuminated with the ECL Plus™ substrate (GE Healthcare) and the X-ray films exposed, according to the manufacturer's instructions.

RAW 264.7 cells were cultured in the absence or presence of LPS (1 µg/ml). Some cells were co-incubated with graded concentrations of XJB-5-131. After 48 or 72 of incubation, culture supernatants were harvested and assayed for the presence of HMGB1 by Western blotting. Since necrotic cells release large amounts of HMGB1 (Scaffidi P, Misteli T, Bianchi M E. Release of chromatin protein HMGB1 by necrotic cells triggers inflammation. Nature 2002, 418:191-195), a lysate of RAW 264.7 cells ("RCL") was used as positive control. When RAW 264.7 macrophage-like cells were incubated with LPS, HMGB1 was secreted into the medium (FIG. 4). Addition of XJB-5-131 inhibited LPS-induced HMGB1 secretion in a concentration-dependent fashion. Results depicted are representative of an experiment, which was repeated four times with similar findings.

Example 4

Effect of Pre-Treatment with XJB-5-13 Ion Nitric Oxide Secretion In Vivo

Animal Studies.

All experiments using mice followed the guidelines for the use of experimental animals of the U.S. National Institutes of Health and were approved by the Institutional Animal Care and Use Committee at the University of Pittsburgh. Male specific pathogen-free C57B1/6J mice (Charles River Laboratories, Wilmington, Mass.), weighing 20-25 g, were housed in a temperature-controlled environment with a 12-h light/dark cycle. Animals had free access to food and water. Randomly assigned animals were challenged with intraperitoneal *Escherichia coli* 0111:B4 LPS (15 mg/kg) dissolved in saline solution (3 mg/ml). Non-endotoxemic control animals received the saline vehicle alone. Mice challenged with LPS were randomized to receive XJB-5-131 (2 µmol/kg) or its vehicle, a 67:33 (v/v) mixture of dimethyl sulfoxide (DMSO) and normal saline, 60 min prior to LPS injection. All mice were euthanized 24 h after being injected with LPS or the normal vehicle.

Blood and Tissue Samples.

Twenty-four hours after LPS stimulation, mice were anesthetized with intraperitoneal pentobarbital (50 mg/kg). Under a deep plane anesthesia, a thoracotomy was performed and blood was withdrawn via cardiac puncture. Blood was centrifuged (4° C., 800 g, 5 min) and serum was retrieved. Liver, heart, lung and kidney samples were harvested and immediately frozen in liquid nitrogen. Specimens were stored at −80° C. until analysis.

Mice were pretreated with XJB-5-131 (n=15) or vehicle (n=19). Mice were randomly pretreated with a solution containing XJB-5-131 (2 µmol/kg) or a similar volume (2 ml/kg) of vehicle, a 67:33 (v/v) mixture of DMSO and normal saline. After one hour, animals were challenged with an intraperitoneal injection of LPS (15 mg/kg). Control animals (n=18) were not injected with LPS or the XJB-5-131 containing solution. Animals were euthanized 24 h after LPS injection and blood was obtained by cardiac puncture. As shown in FIG. 5, injection of LPS was associated with a significant increase in plasma $NO_2^-$ plus $NO_3^-$ levels relative to the levels measured in control mice. Intraperitoneal administration of XJB-5-131 attenuated this in vivo response by decreasing .NO production in LPS stimulated mice, where concentration of nitrites within blood plasma was: 41.8±7.0 nM for control; 321.8±70.1 nM for LPS-challenged mice; and 179.5±34.6 nM for mice pre-treated with XJB-5-131 and then challenged with LPS, $p<0.05$).

Example 5

Effect of Pre-Treatment with XJB-5-131 on Expression of iNOS In Vivo

Mice were randomly pretreated with a solution containing XJB-5-131 (2 µmol/kg) or a similar volume (2 ml/kg) of vehicle, a 67:33 (v/v) mixture of DMSO and normal saline. After 1 h, animals were challenged with an intraperitoneal injection of LPS (15 mg/kg). Control animals were not injected with LPS or the XJB-5-131 containing solution. Animals were euthanized 24 h after LPS injection, and samples of hepatic tissue were harvested and snap frozen. Subsequently, iNOS mRNA expression was measured, using quantitative real-time RT-PCR. Injection of LPS was associated with a significant increase in hepatic iNOS mRNA expression in all organs studied. As shown in FIG. 6, the administration of XJB-5-131 attenuated iNOS expression in liver samples.

Having described this invention above, it will be understood to those of ordinary skill in the art that the same can be performed within a wide and equivalent range of conditions, formulations and other parameters without affecting the scope of the invention or any embodiment thereof. Any terms, phrases, disclosure provided in any reference incorporated herein by reference that is contradictory or otherwise inconsistent with any terms, phrases or disclosure presented herein is to be interpreted as stated herein.

We claim:

1. A method of inhibiting expression of nitric oxide, high mobility group protein B1, or inducible nitric oxide synthase comprising administering to a patient in need thereof a mitochondria-targeted electron scavenger chosen from one of

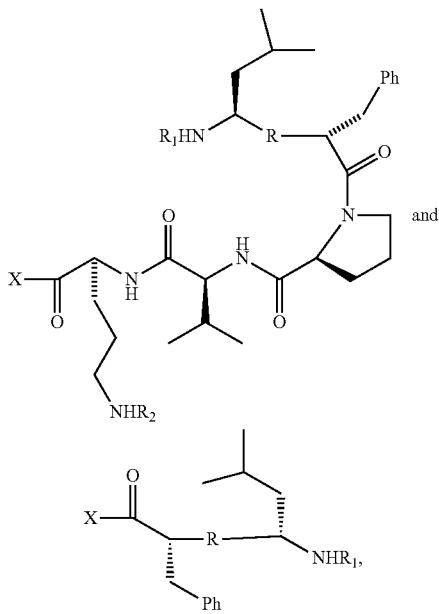

wherein $R_1$ is H or an acyl group, $R_2$ is H or an acyl group, and R is one of cyclopropane, -(E)-CH=CH—, and -(E)-CH=C(CH$_3$) or an isostere or stereoisomer thereof, or pharmaceutically acceptable salt of any of the above, and wherein X is a free radical scavenging group.

2. The method of claim 1, wherein the mitochondria-targeted electron scavenger is acylated.

3. The method of claim 1, wherein the patient is human.

4. The method of claim 1, wherein the mitochondria-targeted electron scavenger is administered to the patient parenterally.

5. The method of claim 1, wherein the mitochondria-targeted electron scavenger is administered to the patient orally.

6. The method of claim 1, wherein the free radical-scavenging group comprises a nitroxide group.

7. The method of claim 6, wherein the free radical-scavenging group comprises 2,2,6,6-tetramethylpiperidine-N-oxyl.

8. The method of claim 6, wherein the free radical-scavenging group comprises 4-hydroxy-2,2,6,6-tetramethylpiperidine-N-oxyl.

9. The method of claim 6, wherein the free radical-scavenging group comprises 4-amino-2,2,6,6-tetramethylpiperidine-N-oxyl.

10. The method of claim 1, wherein the mitochondria-targeted electron scavenger comprises a β-turn motif.

11. The method of claim 10, wherein the β-turn motif comprises an alkene bond.

12. The method of claim 11, wherein the alkene bond is an (E)-alkene bond.

13. The method of claim 10, wherein the β-turn motif comprises a cyclopropane ring.

14. The method of claim 1, wherein the mitochondria-targeted electron scavenger comprises one or more N-acylated amino acids.

15. The method of claim 14, wherein the amino acid is acylated with one or more of the following acylating agents: aryloxycarbonyl agents, including benzyloxycarbonyl (Cbz) and fluorene-9-methyloxycarbonyl (FMOC) agents; and alkyloxycarbonyl agents, including tert-butoxycarbonyl (Boc), methoxycarbonyl, and trichloroethoxycarbonyl agents.

16. The method of claim 14, wherein the N-acylated amino acid is N-Boc-Leu.

17. The method of claim 14, wherein the N-acylated amino acid is Orn(Cbz).

18. The method of claim 1, wherein the mitochondria-targeted electron scavenger comprises

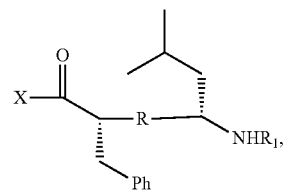

wherein $R_1$ is H or an acyl group and R is the linkage between the Leu and $^D$Phe residues and is one of cyclopropane, -(E)-CH=CH—, and -(E)-CH=C(CH$_3$) or an isostere or stereoisomer thereof, or pharmaceutically acceptable salt of any of the above.

19. The method of claim 18, wherein the mitochondria-targeted electron scavenger is

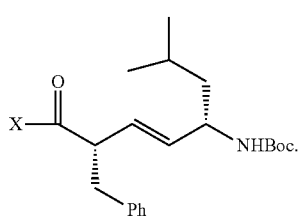

20. The method of claim 1, wherein the mitochondria-targeted electron scavenger comprises

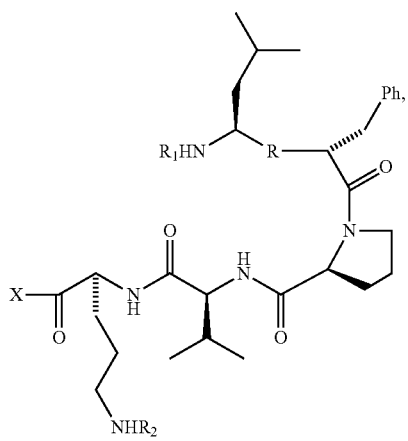

wherein $R_1$ is an acyl group, $R_2$ is an acyl group, and R is the linkage between the Leu and $^D$Phe residues and is one of cyclopropane, -(E)-CH=CH—, and -(E)-CH=C(CH$_3$).

21. The method of claim 20, wherein the mitochondria-targeted electron scavenger is

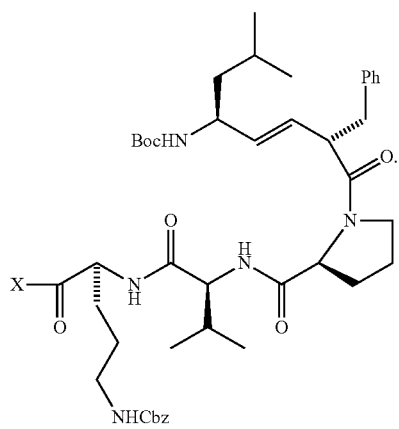

22. The method of claim 1, wherein the mitochondria-targeted electron scavenger comprises

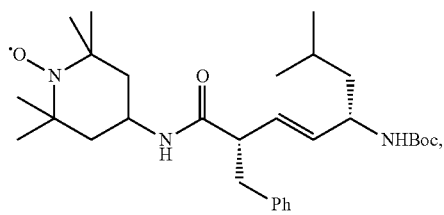

or a pharmaceutically acceptable salt thereof.

23. The method of claim 1, wherein the mitochondria-targeted electron scavenger comprises

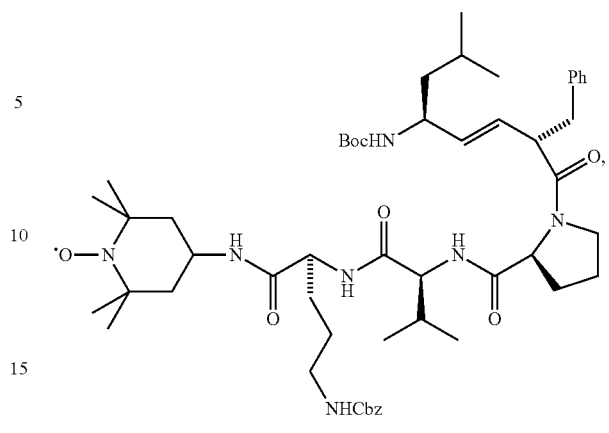

or a pharmaceutically acceptable salt thereof.

24. The method of claim 1, wherein an amount effective to inhibit expression of nitric oxide, high mobility group protein B1, or inducible nitric oxide synthase in the patient is from about 1 μmole/Kg per dose to about 100 μmoles/Kg per dose.

25. A method of inhibiting expression of nitric oxide, high mobility group protein B1, or inducible nitric oxide synthase comprising administering to a patient in need thereof a mitochondria-targeted electron scavenger chosen from one of

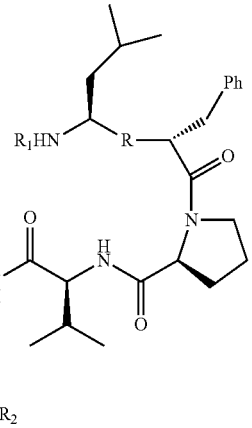

and

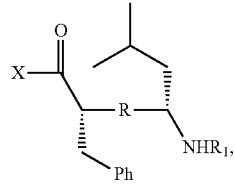

wherein $R_1$ is H or an acyl group, $R_2$ is H or an acyl group, and R is one of cyclopropane, -(E)-CH=CH—, and -(E)-CH=C(CH$_3$)—, and —NH—C(=O)—; or an isostere or stereoisomer thereof, or pharmaceutically acceptable salt of any of the above, and wherein X is a free radical-scavenging group which contains a nitroxide moiety.

26. The method of claim 25, the mitochondria-targeted electron scavenger having the structure

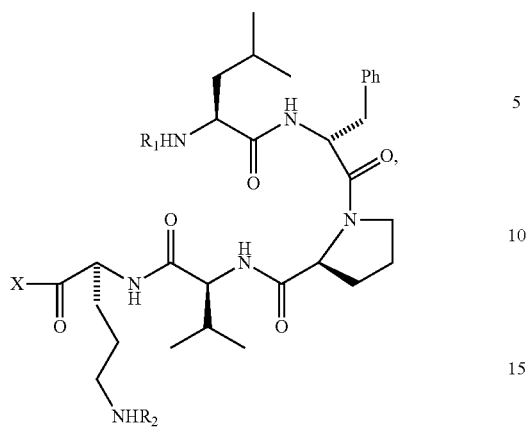
wherein $R_1$ is H or an acyl group and $R_2$ is H or an acyl group.
* * * * *